(12) United States Patent
Chiku et al.

(10) Patent No.: US 8,877,515 B2
(45) Date of Patent: *Nov. 4, 2014

(54) MEASUREMENT KIT AND AN IMMUNOCHROMATOGRAPHY METHOD

(75) Inventors: Hiroyuki Chiku, Kaisei-machi (JP);
Junichi Katada, Kaisei-machi (JP);
Hideyuki Karaki, Minami-Ashigara (JP); Hiroki Terada, Minami-Ashigara (JP)

(73) Assignee: FUJIFILM Corporation, Tokyo (JP)

( * ) Notice: Subject to any disclaimer, the term of this patent is extended or adjusted under 35 U.S.C. 154(b) by 236 days.

This patent is subject to a terminal disclaimer.

(21) Appl. No.: 13/177,971

(22) Filed: Jul. 7, 2011

(65) Prior Publication Data
US 2011/0269247 A1 Nov. 3, 2011

Related U.S. Application Data

(63) Continuation of application No. 12/325,057, filed on Nov. 28, 2008, now Pat. No. 7,998,753.

(30) Foreign Application Priority Data

| Nov. 29, 2007 | (JP) | 2007-308214 |
| Feb. 12, 2008 | (JP) | 2008-029987 |
| Feb. 12, 2008 | (JP) | 2008-029989 |
| Sep. 29, 2008 | (JP) | 2008-249998 |
| Sep. 29, 2008 | (JP) | 2008-249999 |
| Sep. 29, 2008 | (JP) | 2008-250000 |

(51) Int. Cl.
*G01N 33/558* (2006.01)

(52) U.S. Cl.
CPC .......... *G01N 33/558* (2013.01); *Y10S 435/805* (2013.01); *Y10S 435/81* (2013.01); *Y10S 435/97* (2013.01); *Y10S 436/808* (2013.01); *Y10S 436/81* (2013.01)
USPC .......... 436/514; 422/420; 422/425; 422/426; 422/430; 435/287.7; 435/287.8; 435/805; 435/810; 435/970; 436/169; 436/170; 436/808; 436/810

(58) Field of Classification Search
CPC .. G01N 33/525; G01N 33/526; G01N 33/558
See application file for complete search history.

(56) References Cited

U.S. PATENT DOCUMENTS 5,075,078 A 12/1991 Osikowicz et al.
5,401,667 A 3/1995 Koike
(Continued)

FOREIGN PATENT DOCUMENTS

JP 2001-337091 A 12/2001
JP 3496154 B2 2/2004
(Continued)

OTHER PUBLICATIONS

Japanese Office Action dated Sep. 11, 2012 issued in corresponding Japanese Patent Application No. 2008-250000 (with English translation).

(Continued)

*Primary Examiner* — Chris L Chin
(74) *Attorney, Agent, or Firm* — Birch, Stewart, Kolasch & Birch, LLP

(57) ABSTRACT

It is an object of the present invention to provide a measurement kit for developing a first developing solution and a second developing solution from different directions to suppress background noise, and an immunochromatography kit. The present invention provides a measurement kit, which comprises a first developing member for supplying a first developing solution and a second developing member for supplying a second developing solution, wherein the developing direction of the first developing solution is allowed to intersect with the developing direction of the second developing solution, so that development is carried out by developing the first and second developing solutions in different developing directions, and a water absorbent portion is established on the downstream of each of the developing directions.

9 Claims, 14 Drawing Sheets

(56) References Cited

U.S. PATENT DOCUMENTS

| | | | |
|---|---|---|---|
| 5,681,755 A * | 10/1997 | Noppe et al. | 436/525 |
| 5,707,818 A * | 1/1998 | Chudzik et al. | 435/7.93 |
| 5,837,546 A | 11/1998 | Allen et al. | |
| 6,100,099 A | 8/2000 | Gordon et al. | |
| 6,514,769 B2 | 2/2003 | Lee | |
| 6,686,170 B1 | 2/2004 | Flanders et al. | |
| 6,737,277 B1 | 5/2004 | Kang et al. | |
| 6,764,825 B1 | 7/2004 | Wang | |
| 6,998,273 B1 | 2/2006 | Fleming et al. | |
| 7,189,522 B2 | 3/2007 | Esfandiari | |
| 7,270,995 B2 | 9/2007 | Matsushita et al. | |
| 7,297,502 B2 | 11/2007 | Gao et al. | |
| 7,300,761 B2 | 11/2007 | Wang | |
| 7,303,923 B2 | 12/2007 | Hardman et al. | |
| 7,682,801 B2 | 3/2010 | Esfandiari | |
| 7,691,644 B2 | 4/2010 | Lambotte et al. | |

FOREIGN PATENT DOCUMENTS

| | | |
|---|---|---|
| WO | 95/16207 A1 | 6/1995 |
| WO | WO 96-18904 A1 | 6/1996 |
| WO | WO 2006/099191 A2 | 9/2006 |

OTHER PUBLICATIONS

Japanese Office Action dated Feb. 28, 2012 issued in corresponding Japanese Patent Application No. 2008-250000 (with English translation).

Japanese Office Action dated Mar. 13, 2012 issued in corresponding Japanese Patent Application No. 2008-249999 (with English translation).

Japanese Office Action dated Mar. 6, 2012 in corresponding Japanese Patent Application No. 2008-249998 (with English translation).

Tanaka et al.; A novel enhancement assay for immunochromatographic test strips using gold nanoparticles; Anal. Bioanal. Chem.; vol. 385; No. 8; pp. 1414-1420; 2006.

Wang et al.; Development of an immunochromatographic test to detect White Spot Syndrome Virus of shrimp; Aquaculture; vol. 255; No. 1-4; pp. 196-200; 2006.

Japanese Office Action for corresponding Application No. 2008-249998 dated Oct. 2, 2012 (with English translation).

Japanese Office Action for corresponding Application No. 2008-249999 dated Oct. 2, 2012 (with English translation).

Japanese Office Action dated May 7, 2013 issued in corresponding Japanese Patent Application No. 2008-249998 (with English translation).

* cited by examiner

<Comparative Example B-4>

<Example B-4>

|  | Amplification direction | Experimental view | Background concentration measurement value | Background due to remaining gold | Ease of seeing detection line after amplification |
|---|---|---|---|---|---|
| Comparative example 1 | 0 degree | Amplification solution → 0° TL TL CL Water absorbent pad / Sample solution / Amplification solution addition pad   Measurement portion | 0.205 | 0.134 | × High background |
| Example 1 | 30 degrees | Developed at 30 degrees in the manner described in Comparative examples 1 and 2 | 0.190 | 0.119 | △ |
| Example 2 | 45 degrees | Developed at 45 degrees in the manner described in Example 1 | 0.141 | 0.070 | ○ |
| Example 3 | 60 degrees | Developed at 60 degrees in the manner described in Example 1 | 0.121 | 0.050 | ◎ |
| Example 4 | 90 degrees | Developed at 90 degrees in the manner described in Example 1 | 0.101 | 0.030 | ◎ |
| Example 5 | 120 degrees | Developed at 120 degrees in the manner described in Example 1 | 0.112 | 0.041 | ◎ |
| Example 6 | 135 degrees | Developed at 135 degrees in the manner described in Example 1 | 0.125 | 0.054 | ◎ |
| Example 7 | 150 degrees | Developed at 150 degrees in the manner described in Example 1 | 0.131 | 0.060 | ○ |
| Example 8 | 170 degrees | Developed at 170 degrees in the manner described in Example 1 | 0.140 | 0.069 | ○ |
| Comparative example 2 | 180 degrees | 180° | 0.180 | 0.109 | △ |
|  | Only membrane |  | 0.071 |  |  |

FIG.15

| | | Experimental view | Background concentration measurement value | Background due to remaining gold | Ease of seeing detection line after amplification |
|---|---|---|---|---|---|
| Comparative example 1 | 0-degree washing | Washing solution ⇒ 0° TL TL CL Water absorbent pad / Sample solution / Washing solution addition pad / Measurement portion | 0.112 | 0.041 | × High background |
| Example 1 | 30-degree washing | 90° 30° | 0.105 | 0.034 | △ |
| Example 2 | 45-degree washing | Developed at 45 degrees in the manner described in Example 1 | 0.089 | 0.018 | ○ |
| Example 3 | 60-degree washing | Developed at 60 degrees in the manner described in Example 1 | 0.085 | 0.014 | ◎ |
| Example 4 | 90-degree washing | 90° | 0.080 | 0.009 | ◎ Low background and detection line easily seen |
| Example 5 | 120-degree washing | Developed at 120 degrees in the manner described in Example 1 | 0.080 | 0.009 | ◎ |
| Example 6 | 135-degree washing | Developed at 135 degrees in the manner described in Example 1 | 0.083 | 0.012 | ◎ |
| Example 7 | 150-degree washing | Developed at 150 degrees in the manner described in Example 1 | 0.084 | 0.013 | ○ |
| Example 8 | 170-degree washing | Developed at 170 degrees in the manner described in Example 1 | 0.088 | 0.017 | ○ |
| Example 9 | 180-degree washing | 180° | 0.096 | 0.025 | △ |
| | 180-degree washing | | 0.21 | 0.139 | × × High background and detection line not seen |
| | Only membrane | | 0.071 | --- | |

FIG.16

MEASUREMENT KIT AND AN IMMUNOCHROMATOGRAPHY METHOD

This application is a Continuation Application of application Ser. No. 12/325,057 filed on Nov. 28, 2008, [now U.S. Pat. No. 7,998,753 B2 issued Sep. 16, 2011], and to which priority is claimed under 35 U.S.C. 120; and this application claims priority to Application Nos. 2007-308214 filed in Japan on Nov. 29, 2007, 2008-029987 filed in Japan on Feb. 12, 2008, 2008-029989 filed in Japan on Feb. 12, 2008, 2008-250000 filed in Japan on Sep. 29, 2008, 2008-249998 filed in Japan on Sep. 29, 2008 and 2008-249999 filed in Japan on September 29, 2008.

TECHNICAL FIELD

The present invention relates to a measurement kit that allows the developing directions of two developing solutions to intersect with each other and allows the two developing solutions to develop in different directions, and an immunochromatography method using a labeled antibody. Further, the present invention relates to a method for washing a label substance that acts as a background in an immunochromatography method.

BACKGROUND ART

Immunoassays are widely used as methods for qualitatively or quantitatively measuring the presence of an analyte existing in a biological sample such as urine or blood. Of these immunoassays, an immunochromatography method is generally used with high frequency since its implementation is simple and enables short-time measurement.

The competitive reaction and the sandwich reaction are broadly used as immunoreactions to be employed in immunochromatography methods. In particular, the sandwich reaction is mainly employed for an immunochromatography method. In a typical example of the use of the sandwich reaction, the following procedures are performed to detect an analyte comprising an antigen in a sample. (1) A chromatographic medium having a reaction zone is prepared by immobilizing a fine particle as a solid phase fine particle that has been sensitized with an antibody against an antigen that is an analyte on a chromatographic medium or by directly immobilizing the antibody on a chromatographic medium. (2) Meanwhile, a sensitization-target fine particle is prepared by sensitizing a labeled fine particle with an antibody capable of specifically binding to an analyte. (3) The sensitized and labeled fine particle is caused to migrate chromatographically on a chromatographic medium together with a sample.

The thus immobilized antibody is as an immobilized reagent at the reaction zone formed on the chromatographic medium by the above procedures. The sensitized and labeled fine particle specifically binds to the reagent via an antigen that is an analyte. As a result, the presence, absence, or the amount of an analyte in a sample is measured by visually determining the presence, absence, or the degree of signals generated when the sensitized and labeled fine particle is captured at the reaction zone.

In such immunochromatography method, colloidal metal particles or colloidal metal oxide particles, colloidal nonmetal particles, and dye particles are used as fine particles for preparation of labeled fine particles. Moreover, an enzyme such as alkaline phosphatase or peroxidase may be used as a label substance.

In the case of some immunochromatography methods, detection signals are amplified to avoid the problem of no antigens being detected because of low sensitivity (false negative). As such a signal amplification method, there is a method using an enzyme such as alkaline phosphatase or peroxidase as a label substance. There is also a method of detecting an analyte by sensitization using a silver-containing compound and a reducing agent used for silver ions as label substances selected from the group consisting of metal colloid label substances and metal sulfide label substances.

When the signal of a label substance is amplified, there is a case where the signal of another label substance that exists outside the detection line of an immunochromatographic strip is also amplified and background noise is thereby increased. This problem can be solved by allowing an amplification solution to directly come into contact with the detection line or by allowing the amplification solution to come into contact with a portion extremely close to the detection line.

The immunochromatography methods are described in JP Patent Publication (Kokai) No. 2002-202307 A, JP Patent Publication (Kohyo) No. 10-513263 A (1998) and U.S. Pat. No. 7,189,522.

Among bioactive substances or environmental pollutants such as natural products, toxins, hormones, or agricultural chemicals, numerous substances act in ultratrace amounts. Accordingly, instrumental analytical methods capable of performing high-sensitivity analysis have conventionally been widely used for qualitative and quantitative measurement of these substances. However, instrumental analytical methods are poor in specificity, require excessive time for analysis including pretreatment of samples, and are troublesome in operation. Thus instrumental analytical methods are inconvenient for the purpose of rapid and convenient measurements that have been required in recent years. Meanwhile, immunoassays are highly specific and much easier in terms of operation than instrumental analytical methods. Therefore immunoassays have gradually spread in the field of measurement of bioactive substances and environmental pollutants. However, conventional immunoassays such as enzyme immunoassays and latex agglutination assays using 96-well plates do not always provide satisfactory rapidness and convenience for measurement or detection sensitivity.

Another need expected to be enabled is as follows. Achievement of higher sensitivity of tests that currently use relatively invasive samples such as swabs and blood makes it possible to detect very small amounts of analytes contained in relatively low-invasive samples such as snot, mouth wash, and urine. Thus, less burdensome tests of patients can be realized.

In recent years, test kits using an immunochromatography method (hereinafter referred to as an immunochromatography kit) have been used more often in examination of infections that require particularly rapid diagnosis. According to the spread of these kits, patients with infections can be identified by a rapid and convenient method, and subsequent diagnosis and therapy can be conducted immediately and accurately. For example, in an immunochromatography method using the sandwich method, a labeled first antibody capable of specifically binding to an analyte (for example, an antigen) and a sample solution which may possibly contain the analyte are developed on a first insoluble carrier (for example, a nitrocellulose membrane, a glass fiber membrane, a nylon membrane, cellulose membrane, etc.) on which a second antibody capable of specifically binding to the analyte has been immobilized in a specific region. As a result, an immune complex with the analyte is formed in the region on which the second antibody of the first insoluble carrier has been immobilized. The analyte can be measured by detecting a signal such as color development or coloring of a label substance. The label substance to be used herein may be, for example, a protein such as an enzyme, colored latex particles, metal colloids, or carbon particles.

The immunochromatography method requires neither massive facilities nor instruments for determination and measurement. Furthermore, the immunochromatography method is simple in operation and promptly gives measurement results by introducing a sample solution dropwise which may possibly contain an analyte and leaving it for approximately 5 to 10 minutes. For this reason, this technique is used widely as a convenient, rapid, and highly specific method for determination and measurement in many scenarios, such as for clinical examination in hospitals and in assays in laboratories.

Among bioactive substances or environmental pollutants such as natural products, toxins, hormones, and agricultural chemicals, many substances exert effects in ultratrace amounts that are undetectable by conventional common immunochromatography methods. Therefore, there are demands for development of rapid, convenient, and highly sensitive immunochromatography methods for such substances.

As immunochromatography methods for achieving high sensitivity by signal amplification, an amplification method using enzymes (Japanese Patent No. 3237540, and Japanese Patent No. 3309977), a method involving chemical amplification (Japanese Patent No. 3886000), and a method involving silver amplification (JP Patent Publication (Kokai) No. 2002-202307 A) have been known. When a signal is amplified, noise caused by a label substance existing in the background is also simultaneously amplified. Thus, in order to eventually increase detection sensitivity, it is particularly necessary to decrease noise caused by such a label substance existing in the background. In Japanese Patent No. 3309977, a washing solution is supplied to wash such a label substance in the background in an enzyme amplification immunography method. However, this washing operation is not sufficient for carrying out an examination with sensitivity higher than that of a common enzyme amplification immunochromatography method, towards which the present system is directed.

As a method for increasing the sensitivity of an immunochromatography method using a metal colloid as a label substance, a silver amplification method has been known (JP Patent Publication (Kokai) No. 2002-202307 A). In JP Patent Publication (Kokai) No. 2002-202307 A, after a solution has been supplied, another solution used for silver amplification is added dropwise to a detection line portion to carry out amplification, thereby achieving high sensitivity. However, if high sensitivity that is above a certain level is required, an increase in noise caused by a label substance existing in the background becomes problematic.

Like the present system, when signal amplification is carried out using an amplification solution used for silver amplification that enables amplification at a level higher than that of the solution used in silver amplification disclosed in JP Patent Publication (Kokai) No. 2002-202307 A, if detection sensitivity is intended to be increased, further noise reduction is necessary.

Under the present circumstances, in any case, a technique of sufficiently decreasing noise, which is required when signal amplification is carried out using an amplification solution used for silver amplification that enables high-level amplification, has not yet been introduced.

DISCLOSURE OF THE INVENTION

Thus, it is an object of the present invention to provide a measurement kit for developing a first developing solution and a second developing solution from different directions to suppress background noise, and an immunochromatography kit.

Further, when a signal is amplified by an immunochromatography method, this method is problematic in that a long time is required for amplification and in that unevenness is found after amplification. It is another object of the present invention to provide an immunochromatography method, which reduces an amplification time and also decreases unevenness found after amplification.

Realization of high sensitivity has been required for immunoassay methods, and such high sensitivity has been achieved by silver amplification. In general, when the concentration of a test sample collected at the initial stage of infectious disease is extremely low, or when a test sample contained in a trace amount in a relatively low invasive analyte such as a running nose, a gargle water or urine is to be detected, higher sensitivity is required. When a signal is amplified, noise caused by a label substance existing in the background is also simultaneously amplified. Thus, in order to eventually increase detection sensitivity, it is necessary to decrease noise caused by such a label substance existing in the background. It is further another object of the present invention to provide a highly sensitive immunochromatography method in which noise caused by a label substance existing in the background is decreased.

As a result of intensive studies directed towards achieving the aforementioned object, the present inventors have devised a method for allowing a developing solution to directly come into contact with a detection line or allowing the developing solution to come into contact with a portion extremely close to the detection line, thereby completing the present invention. In the present invention, water absorbent portions are disposed downstream of a portion on which the first developing solution is developed and also downstream of a portion on which the second developing solution is developed, so that the development of the solutions can be reliably and rapidly carried out.

Further, as a result of intensive studies directed towards achieving the aforementioned object, the present inventors have found that, after a sample has been added dropwise to an immunochromatographic strip using a metal colloid label substance and a metal sulfide label substance and it has been developed thereon, amplification is carried out by developing the sample and a silver amplification solution in each different directions, so that the amplification solution is allowed to directly come into contact with a detection line or it is allowed to come into contact with a zone extremely close to the detection line, and that, as a result, a reduction in the amplification time of signal and a decrease in unevenness found after amplification can be achieved. The present invention has been completed based on the aforementioned findings.

Still further, in the present invention, it was found that a washing solution is developed to wash a label substance non-specifically remaining in a carrier, such that an angle of 45 to 170 degrees can be made between the developing direction of an analyte and the developing direction of the washing solution, so as to provide a highly sensitive immunochromatography method in which noise caused by a non-specific label substance can be decreased. The present invention has been completed based on the aforementioned findings.

According to the present invention, there are provided the following inventions (1) to (3).
(1) The First Invention
The present invention provides a measurement kit, which comprises a first developing member for supplying a first developing solution and a second developing member for supplying a second developing solution, the measurement kit being characterized in that the developing direction of the first developing solution is allowed to intersect with the developing direction of the second developing solution, so that development is carried out by developing the first and second developing solutions in different developing directions, and in that a water absorbent portion is established on the downstream of each of the developing directions.

Preferably, a binding substance that binds to an analyte is held at the intersection zone between the developing direction of the first developing solution and the developing direction of the second developing solution of the member for supplying the first developing solution.

Preferably, the angle between the developing direction of the first developing solution and the developing direction of the second developing solution is 45 to 170 degrees.

Preferably, the angle between the developing direction of the first developing solution and the developing direction of the second developing solution is 60 to 150 degrees.

Preferably, the angle between the developing direction of the first developing solution and the developing direction of the second developing solution is 90 degrees (vertical).

Preferably, the second developing solution is developed, after the first developing solution has been developed.

Preferably, the first developing solution is a solution containing an analyte and the second developing solution is a solution containing an amplification solution or a portion thereof.

Preferably, the first developing member is an insoluble carrier.

Preferably, the insoluble carrier is a porous carrier.

Preferably, the measurement kit comprises a label substance modified with a second substance that binds to the analyte or with a compound having a portion similar to the analyte.

Preferably, the label substance is a metal colloid.

The present invention further provides an immunochromatography method, which comprises: developing an analyte and a label substance modified with a first binding substance that binds to the analyte on a first insoluble carrier in a state where the analyte and the label substance are mixed; and capturing the analyte and the label substance at a reaction zone on the first insoluble carrier having a second binding substance that binds to the analyte or a substance having ability to bind to the first binding substance that binds to the analyte, so as to detect the analyte, the method being characterized in that it comprises detecting the analyte by sensitization using an amplification solution that contains a silver-containing compound and a reducing agent used for silver ions, and in that the developing direction of the analyte intersects with the developing direction of the amplification solution and the development is carried out while setting the developing direction of the analyte and the developing direction of the amplification solution at different directions.

Preferably, the first binding substance and/or the second binding substance is an antibody.

Preferably, the angle between the developing direction of the analyte and the developing direction of the amplification solution is 45 to 170 degrees.

Preferably, the angle between the developing direction of the analyte and the developing direction of the amplification solution is 60 to 150 degrees.

Preferably, the angle between the developing direction of the analyte and the developing direction of the amplification solution is 90 degrees (vertical).

Preferably, the insoluble carrier is a porous carrier.

Preferably, the porous carrier is nitrocellulose.

Preferably, a label substance having a mean particle size of 1 µm to 20 µm is detected.

Preferably, the reaction time required for the sensitization using the silver-containing compound and the reducing agent used for silver ions is within 7 minutes.

Preferably, the number of label substances at a detection zone is $1\times10^6/mm^3$ or less.

Preferably, the label substance is a metal colloid.

(2) The Second Invention

The present invention provides an immunochromatography method, which comprises: developing an analyte and a label substance modified with a first binding substance that binds to the analyte on an insoluble carrier in a state where the analyte and the label substance are mixed; and capturing the analyte and the label substance at a reaction zone on the insoluble carrier having a second binding substance that binds to the analyte or a substance having ability to bind to the first binding substance that binds to the analyte, so as to detect the analyte, the method being characterized in that it comprises detecting the analyte by sensitization using an amplification solution that contains a silver-containing compound and a reducing agent used for silver ions, and in that the development is carried out while setting the developing direction of the analyte and the developing direction of the amplification solution at different directions.

Preferably, the angle between the developing direction of the analyte and the developing direction of the amplification solution is 45 to 170 degrees.

Preferably, the angle between the developing direction of the analyte and the developing direction of the amplification solution is 60 to 150 degrees.

Preferably, the angle between the developing direction of the analyte and the developing direction of the amplification solution is 90 degrees (vertical).

Preferably, the first binding substance and/or the second binding substance is an antibody.

Preferably, the insoluble carrier is a porous carrier.

Preferably, the porous carrier is nitrocellulose.

Preferably, the label substance is a metal colloid.

Preferably, the label substance is gold, silver, platinum, or a compound thereof.

Preferably, the label substance having a mean particle size of 1 µm to 20 µm is detected.

Preferably, the reaction time required for the sensitization using the silver-containing compound and the reducing agent used for silver ions is within 7 minutes.

Preferably, the number of label substances at a detection zone is $1\times10^6/mm^3$ or less.

(3) The Third Invention

The present invention provides an immunochromatography method, which comprises: developing an analyte and a label substance modified with a first binding substance that binds to the analyte or a label substance modified with a compound having a portion similar to the analyte on a first insoluble carrier in a state where the analyte and the label substance are mixed; and capturing the analyte and the label substance at a reaction zone on the first insoluble carrier having a second binding substance that binds to the analyte or a substance having ability to bind to the first binding substance that binds to the analyte, so as to detect the analyte, the method being characterized in that, after the analyte has been developed, a washing solution is developed on the carrier for washing such that an angle of 45 to 170 degrees can be made between the developing direction of the analyte and the developing direction of the washing solution, and the analyte is detected.

Preferably, the first binding substance and/or the second binding substance is an antibody.

Preferably, the insoluble carrier is a porous carrier.

Preferably, the first insoluble carrier is a porous carrier.

Preferably, the label substance comprises a metal colloid.

Preferably, the metal colloid is a gold colloid.

Preferably, the washing time is 10 to 300 seconds.

Preferably, the washing solution does not comprise a label substance.

Preferably, sensitization is carried out with an amplification solution that contains a silver-containing compound and a reducing agent used for the silver.

Preferably, the amplification solution contains bivalent iron ions.

Preferably, the washing solution contains a reducing agent for silver or a compound containing silver.

The present invention further provides an immunological test kit, which is used in application of the immunochromatography method of the present invention, which comprises at least (a) a first insoluble carrier, (b) a label substance modified with a first binding substance that binds to an analyte or with a compound having a portion similar to the analyte, (c) a label substance modified with a second binding substance that binds to an analyte or with a compound having a portion similar to the analyte, (d) a washing solution, and (e) a second insoluble carrier laminated on the first insoluble carrier.

The present invention further provides an immunological test kit, which is used in application of the immunochromatography method of the present invention, which comprises at least (a) a first insoluble carrier having a washing solution-adding portion, wherein a straight line that connects the adding portion and a reaction zone having a label substance modified with a second binding substance or with a compound having a portion similar to an analyte intersects with a straight line on which the analyte is developed at the reaction zone, (b) a label substance modified with a first binding substance that binds to the analyte or with a compound having a portion similar to the analyte, (c) a label substance modified with a second binding substance that binds to an analyte or with a compound having a portion similar to the analyte, and (d) a washing solution.

After a sample has been added dropwise to an immunochromato graphic strip using a metal colloid label substance and a metal sulfide label substance and it has been developed thereon, if sensitization is carried out using an amplification solution containing the aforementioned silver, it is necessary to allow the aforementioned label substance to come into contact with the aforementioned amplification solution. This time, there may be cases where the signals of the aforementioned label substances that exist outside the detection line of the immunochromatographic strip are also amplified and where non-specific amplification occurs. This problem can be solved by allowing an amplification solution to directly come into contact with the detection line or by allowing the amplification solution to come into contact with a portion extremely close to the detection line.

Further, in the present invention, by shortening the distance between the contact area with the amplification solution and the detection line, the amplification time can be reduced, and unevenness found after amplification can also be decreased. Thus, clear measurement results can be obtained in a short time.

Further, in the present invention, in an immunochromatography method, after an analyte has been developed, a washing solution is developed to carry out washing, such that an angle of 45 to 170 degrees can be made between the developing direction of the analyte and the developing direction of the washing solution, so as to decrease noise, thereby enabling highly sensitive detection. In particular, the signal of a label substance of a detection line portion is amplified using an amplification solution after such a washing operation, so that highly sensitive detection can be achieved. In the present invention, a washing solution and an amplification solution may be supplied, separately. However, they may also be supplied simultaneously in the form of a single liquid. Moreover, other advantages of the present invention are that a time required for a washing solution passing through an insoluble carrier becomes shorter than in the case of washing from an angle of 0 degree, for example, by developing the washing solution for washing such that an angle of 45 to 170 degrees can be made between the developing direction of the analyte and the developing direction of the washing solution, and that a washing effect per unit time is high and thus a washing time required for a necessary level of washing becomes short, and as a result, an examination time also becomes short.

BRIEF DESCRIPTION OF THE DRAWINGS

FIG. 15 shows the relationship between the angle made between the developing direction of the amplification solution and the developing direction of the sample solution and the background due to a non-specifically remaining label substance.

FIG. 16 shows the relationship between the angle made between the developing direction of the washing solution and the developing direction of the sample solution and the background due to a non-specifically remaining label substance and the ease of seeing the detection line after amplification.

PREFERRED EMBODIMENT OF THE INVENTION (As to the First Invention)

In the present invention, the first developing solution is used to mean a solution that contains a substance to be detected, such as a test sample, and the second developing solution is used to mean an amplification solution, a solution that contains a substance for enhancing the signal of a label substance, such as an enzyme substrate, a solution for washing, or a solution that contains a portion of components necessary for amplification.

The materials of the first developing member and second developing member are not particularly limited, as long as the members are capable of supplying developing solutions by capillary action. A porous thin film, a fiber, a polymer having a flow channel consisting of a fine groove, a member consisting of glass, etc. can be used. As a porous thin film and a fiber, a nitrocellulose membrane, a cellulose membrane, an acetylcellulose membrane, a polysulfone membrane, a polyethersulfone membrane, a nylon membrane, a glass fiber, a non-woven fabric, a fabric, a thread, etc. are preferable.

Figure 1:
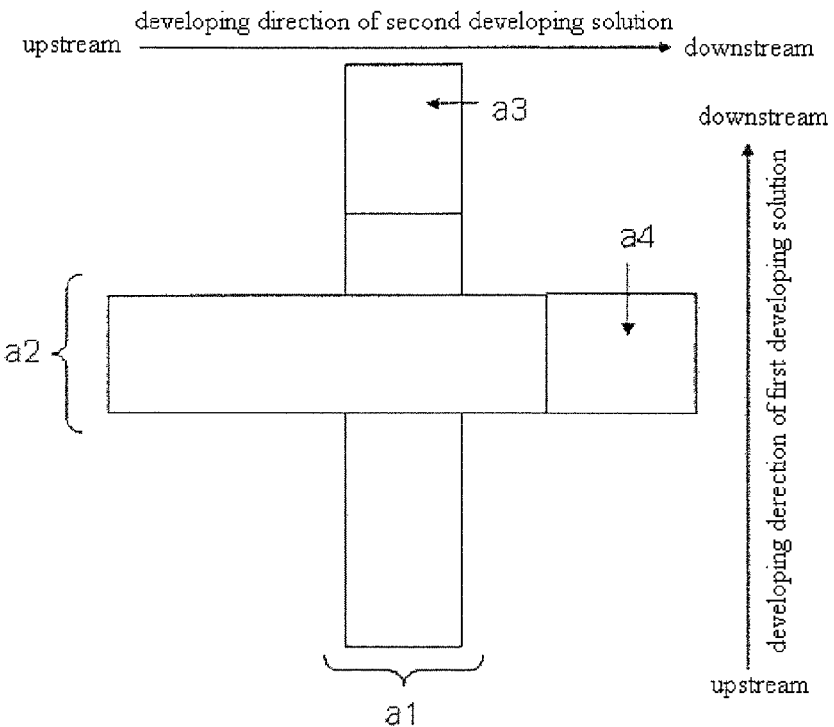
FIG. 1 is a plan view schematically showing two embodiments of an immunochromatography kit that can be used in the present invention.
Figure 1:
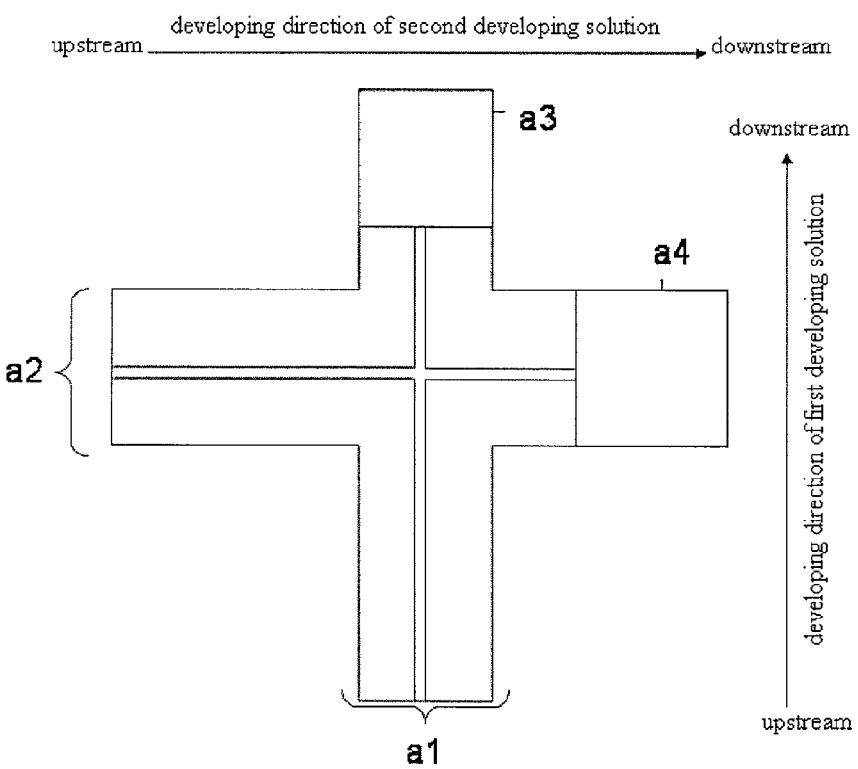

In FIG. 1, a first developing solution is added upstream of a developing member a1 for developing the first developing solution, and a second developing solution is added upstream of a developing member a2 for developing the second developing solution. On the other hand, water absorbent portions a3 and a4 are established downstream of the developing members a1 and a2, respectively. The developing member a1 intersects with the developing member a2, and the developing faces of the two developing solutions overlap each other in the contact areas of the two developing members. Thereby, the developing solutions can be transferred between the two developing members. As shown in the lower view of FIG. 1, a member made of a polymer or a glass having a flow channel consisting of a fine groove may also be used as a developing member, if it has the same above structure.

Figure 2:
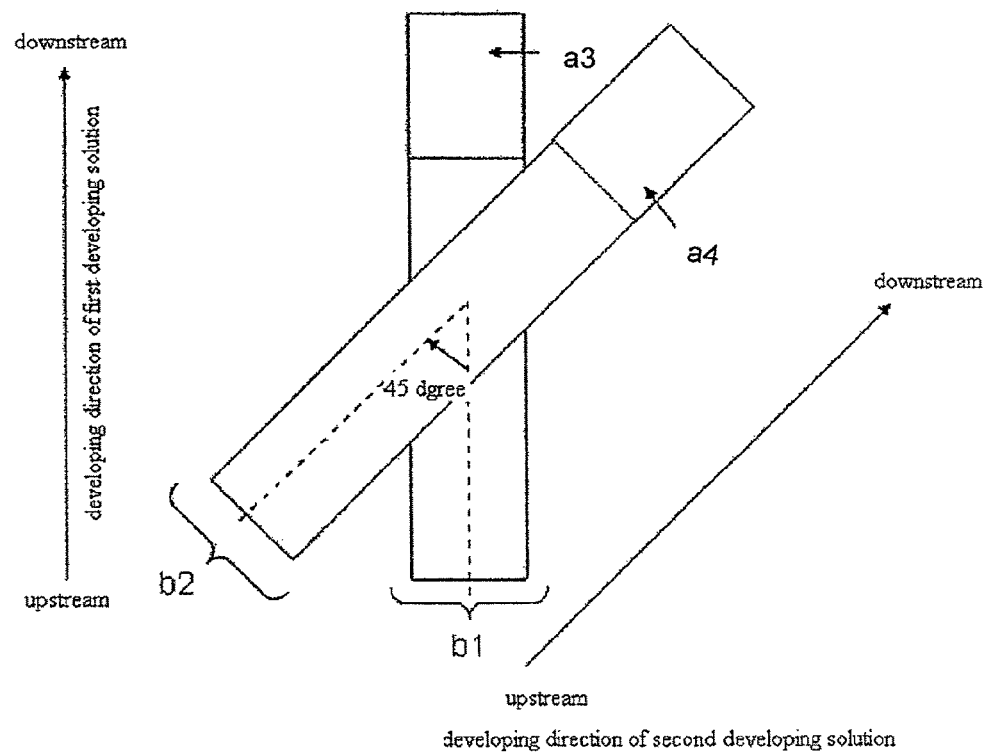
FIG. 2 is a plan view schematically showing an embodiment of an immunochromatography kit that can be used in the present invention.

Moreover, for example, as shown in FIG. 2, the angle made between a developing member b1 for developing a first developing solution and a developing member b2 for developing a second developing solution may be 45 degrees, with respect to each developing direction. In this case also, water absorbent portions a3 and a4 are established downstream of the developing members b1 and b2, respectively. The developing member b1 intersects with the developing member b2, and the developing faces of the two developing solutions overlap each other in the contact areas of the two developing members.

Figure 3:
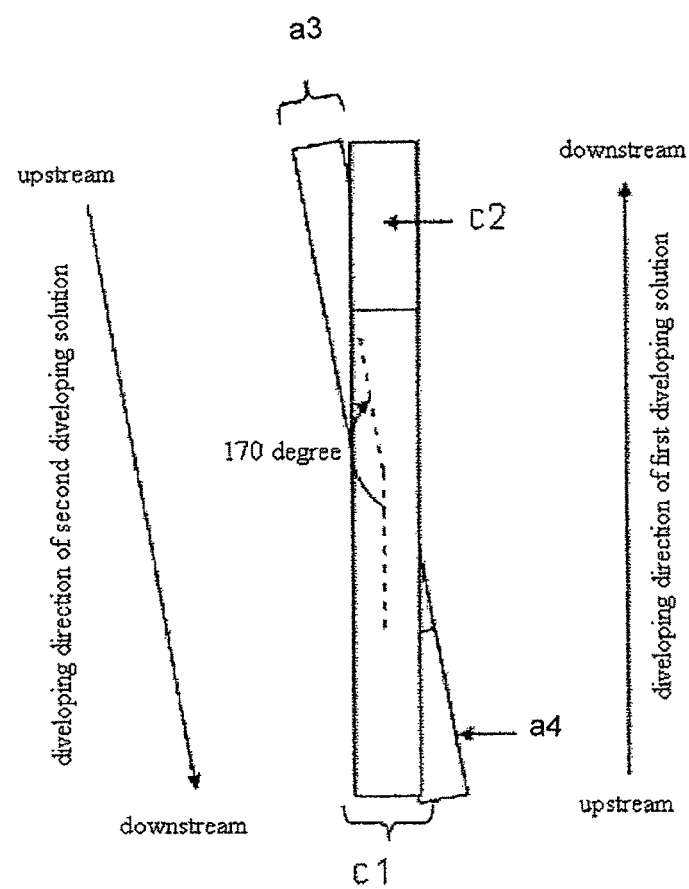
FIG. 3 is a plan view schematically showing an embodiment of an immunochromatography kit that can be used in the present invention.

Similarly, for example, as shown in FIG. 3, the angle made between a developing member c1 for developing a first developing solution and a developing member c2 for developing a second developing solution may be 170 degrees, with respect to each developing direction. In this case also, water absorbent portions a3 and a4 are established downstream of the developing members c1 and c2, respectively. The developing member c1 intersects with the developing member c2, and the developing faces of the two developing solutions overlap each other in the contact areas of the two developing members. The angle made between a developing member for developing a first developing solution and a developing member for developing a second developing solution is not particularly limited, as long as it is between 45 and 170 degrees with respect to each developing direction.

Figure 4:
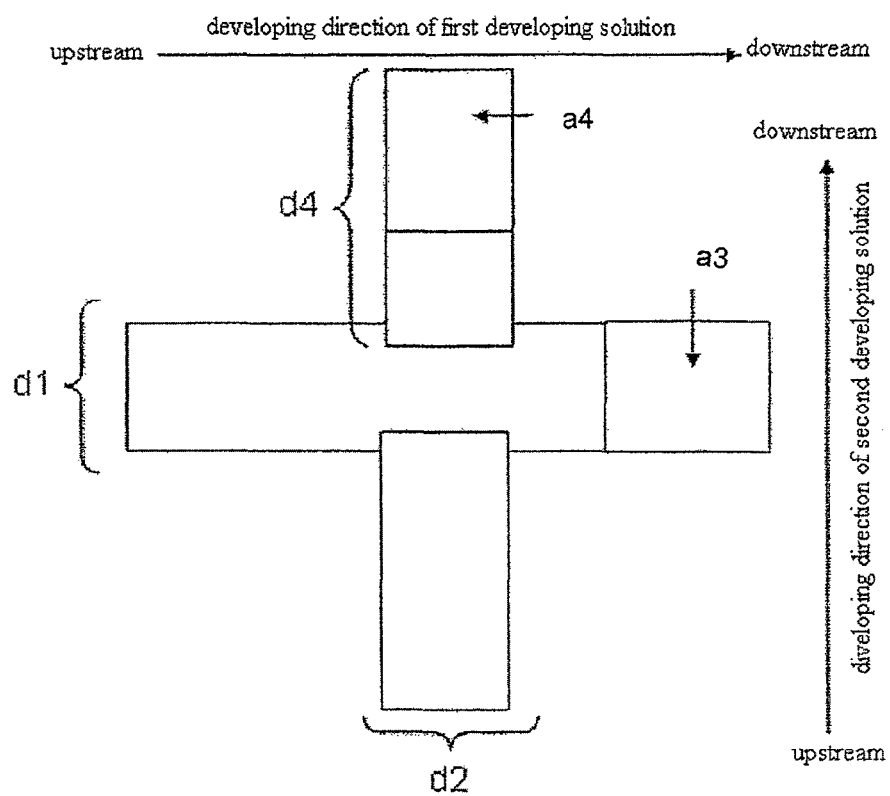
FIG. 4 is a plan view schematically showing an embodiment of an immunochromatography kit that can be used in the present invention.

With regard to a developing member d1 for developing a first developing solution and a developing member d2 for developing a second developing solution, each member may be divided into two or more members. For example, as shown in FIG. 4, in contrast to an integral-type developing member d1 and an integral-type water absorbent portion a3, a developing member for developing a second developing solution may be divided into a member d2 comprising a portion for developing the second developing solution and a member d4 comprising a water absorbent portion a4 for absorbing the second developing solution. In this case also, the angle made between the developing member for developing the first developing solution and the developing member for developing the second developing solution is not particularly limited, as long as it is between 45 and 170 degrees with respect to each developing direction.

Depending on the amount of the first developing solution, or in order to control the developing rate, the water absorbent portion a3 may be optimally adjusted by changing the volume, material, and form thereof. Any type of material, such as a cellulose filter, a non-woven fabric, a fabric or cellulose acetate can be used, as long as it can be used as a water absorbent material. What is called a water absorbent polymer such as a sodium polyacrylate compound may also be used.

Furthermore, the water absorbent portion a3 may be identical to the water absorbent portion a4 for the second developing solution. Otherwise, in order to optimize each development, these absorbent portions may also have different material, form, and volume.

Figure 5:
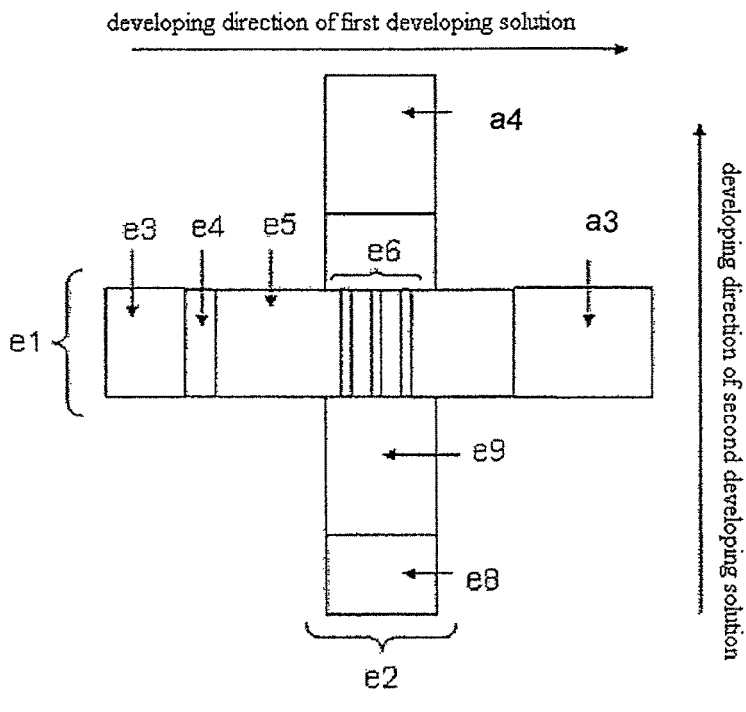
FIG. 5 is a plan view schematically showing two embodiments of an immunochromatography kit that can be used in the present invention.
Figure 5:
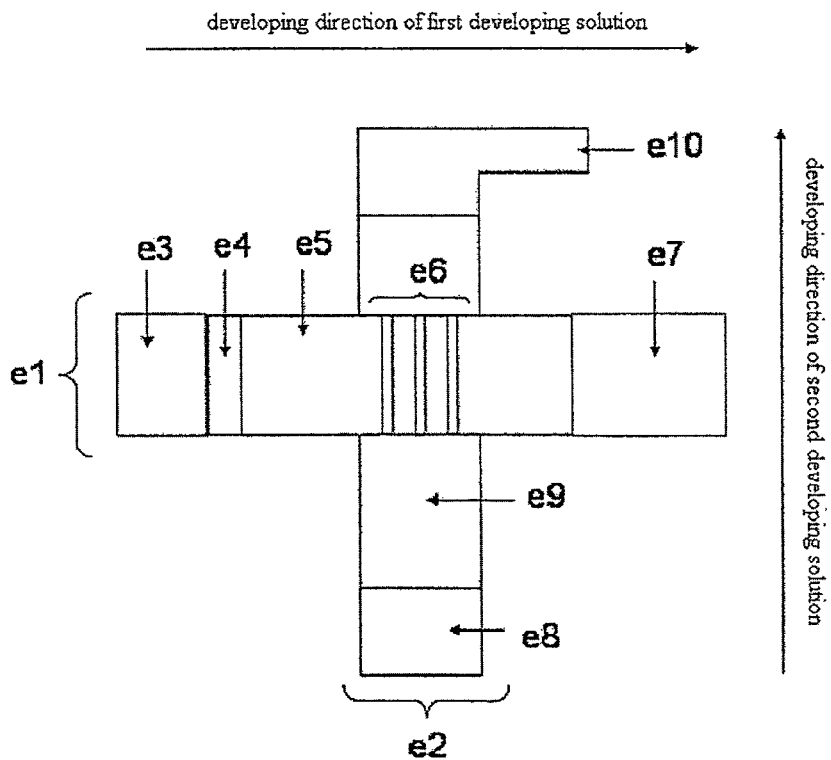

Further, in the present patent application, the present invention may be applied to an immunochromatography kit. For example, as shown in FIG. 5, the present invention provides a kit in which an immunochromatographic strip e1 for developing a sample intersects with an amplification solution-developing strip e2 for developing an amplification solution, such that faces on which developing solutions are supplied overlap. First, when a sample is added dropwise to a sample addition pad e3, a label compound is discharged by developing the sample on a label compound-holding pad e4. When both a label compound and a detected product exist, they form a complex. This complex is developed on a chromatographic carrier e5, and it is then captured by a detection portion e6 that holds a second binding substance that binds to an analyte or a compound having a portion similar to the analyte. This development of solution is continuously carried out by absorbing water at a water absorbent portion a3. Subsequently, when an amplification solution is added to an amplification solution addition pad e8 of the amplification solution-developing strip e2, the amplification solution is developed on an amplification solution-developing carrier e9 and it is also developed on the detection zone e6 at a zone that intersects with the strip e2, so that the captured label substance can be amplified and detected. The development of the amplification solution is continuously carried out by absorbing water at a water absorbent portion a4 of the strip e2.

In order to sufficiently develop the first developing solution, the volume of the water absorbent portion a3 is preferably 1 to 100,000 $mm^3$, and more preferably 1 to 1,000 $mm^3$. The volume of the water absorbent portion is determined depending on the amount of a developing solution to be absorbed, the time required for the development, and the flow rate required for the development. In the present invention, it is necessary to develop a second developing solution after the development of a first developing solution has been terminated to a certain extent. In general, the amount of the first developing solution is approximately 10 to 500 $mm^3$. Thus, it is considered preferable that the aforementioned volume be approximately ⅒ to 2 times of the amount of the first developing solution.

In addition, in order to sufficiently develop the second developing solution, the volume of the water absorbent portion a4 is preferably 1 to 100,000 mm³. The term "the volume of the water absorbent portion" is used herein to mean a volume obtained based on the length of each side of the water absorbent portion measured.

The volume ratio (a4 volume)/(a3 volume) between the water absorbent portion a4 and the water absorbent portion a3 is preferably 0.01 to 100, and more preferably 0.1 to 10. If the volume of the water absorbent portion e10 is too small when compared with the volume of the water absorbent portion a3, it is difficult to completely terminate the development of a solution onto the water absorbent portion a3. Thus, when the solution is to be developed onto the water absorbent portion a4, the amount of the solution developed in the a3 direction is inevitably larger, and thus the development of the solution cannot be properly carried out in a desired direction. If the volume of the water absorbent portion a4 is too large when compared with the volume of the water absorbent portion a3, components that have been once absorbed into a3 are unfavorably developed in the direction of the water absorbent portion a4 due to backflow.

The form of such water absorbent portion shown in the figure is rectangular. However, in order to reduce the size of a kit, as shown in the lower view of FIG. 5, the water absorbent portion may have forms other than a rectangle.

When the present invention is applied to immunochromatography as well, the angle between the developing direction of an analyte and the developing direction of an amplification solution is not particularly limited, as long as it is between 45 and 170 degrees.

(As to the Second Invention)

When sensitization is carried out using an amplification solution containing the aforementioned silver, after a sample has been added dropwise to an immunochromatographic strip using a metal colloid label substance and a metal sulfide label substance and it has been developed thereon, it is necessary to allow the aforementioned label substance to come into contact with the aforementioned amplification solution. As a method of allowing the label substance to come into contact with the amplification solution, there are the following methods: (1) the aforementioned amplification solution is added dropwise to a zone at which the aforementioned label substance is present; (2) the immunochromatographic strip as a whole is immersed in the aforementioned amplification solution; (3) a portion of the immunochromatographic strip is allowed to come into contact with the aforementioned amplification solution, so that the amplification solution can be absorbed by capillary action; and the like. However, in the case of the aforementioned steps (1) and (2), if the immunochromatographic strip contains water, even if the strip is allowed to come into contact with the aforementioned amplification solution, it takes time to reach an equilibrium, and thus amplification requires a long time. Hence, in order to reduce time for amplification, it is necessary to dry the immunochromatographic strip once. In contrast, in the case of the aforementioned step (3), since liquid existing in the immunochromatographic strip is successively absorbed into a water absorbent pad by capillary action, the liquid is exchanged quickly. As a result, when compared with the aforementioned steps (1) and (2), the time required for sensitization of a label substance can be reduced in the case of the aforementioned step (3).

Moreover, in the case of the aforementioned step (3) as well, if the distance between the contact area of the immunochromatographic strip with an amplification solution and a detection line is long, it takes time for the amplification solution to reach the detection line. As a method of shortening the distance between the contact area of the immunochromatographic strip with the amplification solution and the detection line, there is a method comprising developing a sample and an amplification solution in each different directions. By this method, it becomes possible to allow the amplification solution to directly come into contact with a portion of the detection line or to allow the amplification solution to come into contact with a zone extremely close to the detection line, so that the distance between the contact area with the amplification solution and the detection line can be shortened, thereby succeeding in a reduction in the amplification time.

In the present invention, the angle between the developing direction of the analyte and the developing direction of the amplification solution is not particularly limited, as long as it is between 45 and 170 degrees.

Moreover, when the signal of a label substance is amplified, there are cases where the signal of a label substance existing at a zone other than the detection line of the immunochromatographic strip is also amplified, and where unevenness is found after amplification. This problem can be solved by allowing an amplification solution to directly come into contact with the detection line or by allowing the amplification solution to come into contact with a portion extremely close to the detection line.

The amplification operation of the present invention is carried out after an analyte has been developed. At that time, pads attached to the immunochromatographic strip may be or may not be removed. Further, new pads may be or may not be established downstream of the developing direction of the amplification solution. Furthermore, during such amplification operation, in order to allow the upstream zone of the strip to come into contact with the amplification solution, a portion thereof may be or may not be cut. At that time, new pads may be or may not be established upstream of the strip.

In the immunochromatography method of the present invention, in a detection step, a label substance having a mean particle size between 1 μm and 20 μm can be detected. The mean particle size of the label substance is more preferably between 3 μm and 20 μm when it is detected.

As a method of adjusting the mean particle size of such a label substance when detected to the range of the present invention, there are the following means. Such means may be used singly or in combination. Means 1 involves an amplification time. That is, the longer the amplification time, the larger the particle size that can be obtained. Means 2 involves the level of the reduction ability of a reducing agent. The higher the level of the reduction ability of the reducing agent, the larger the particle size that can be obtained. On the other hand, if the level of the reduction ability is too high, new particles are generated at zones other than the label substance before detection. Thus, careful control is necessary. For example, it is necessary to devise means such as the control of the strength of a reducing agent using the ratio between Fe2+ and Fe3+. Means 3 involves an increase in the concentration of a substance that adheres to the label substance to greaten the size thereof, such as silver ions. The higher the concentration of the aforementioned substance, the larger the particle size that can be obtained. In addition, means 4 involves an amplification temperature. The optimal temperature for amplification is determined depending on the type and amount of the reducing agent, the concentration of a substance that greaten the size of the label substance, etc. It is important that the mean particle size of the label substance when it is detected be adjusted to 1 μm or more to 20 μm or less by the combination of such conditions. It is extremely difficult to adjust the particle size of the label substance when detected to a size of 1 μm or more, which is determined in the present invention, particularly in a short time such as 7 minutes or less. However, the present inventors have conducted intensive studies regarding the aforementioned conditions, and have found a means for stably greatening the mean particle size of a label substance by controlling amplification, thereby completing the present invention relating to an immunochromatography kit for detecting a trace amount of substance.

The reaction time necessary for sensitization using a compound containing silver and a reducing agent used for silver ions is preferably within 7 minutes, more preferably within 5 minutes, and particularly preferably within 90 seconds.

The number of label substances existing at a detection zone is preferably $1 \times 10^6/mm^3$ or less, more preferably $1 \times 10^5/mm^3$ or less, and particularly preferably $1 \times 10^4/mm^3$ or less.

(As to the Third Invention)

(1). Washing Solution

In the present invention, a PBS buffer that contains 1% BSA is used as a washing solution. However, any type of liquid may be used, as long as it is a liquid used for washing a label substance remaining in a membrane, other than those used in an antigen-antibody reaction, namely, a non-specifically remaining label substance.

Only for the purpose of washing remaining gold, it is considered sufficient to wash with water. However, in reality, a labeling compound that has non-specifically interacted with a membrane or a second binding substance immobilized on the membrane should also be washed as much as possible. In this case, pH may be adjusted to increase a washing effect, or a washing solution containing a surfactant component, a protein such as BSA, or a polymeric compound such as polyethylene glycol may be used.

The pH of a washing solution may be adjusted using an acid or a base (preferably, an acid). Examples of an acid that can be used in the present invention include organic acids such as citric acid, ascorbic acid or acetic acid, and inorganic acids such as hydrochloric acid, nitric acid or sulfuric acid. Moreover, in order to keep such pH constant, a buffer solution may also be used. The washing solution may be identical to an amplification solution as described below. In such a case, the pH of the below-described amplification solution is pH 1 to 1.5.

A washing solution used for washing non-specific adsorption is preferably separated from the isoelectric point(s) of a first binding substance and/or a second binding substance. In addition, the isoelectric point of a common antibody is around the neutral range. Thus, pH in the case of using an antibody as a first or second binding substance is preferably pH 0.5 to pH 9, more preferably pH 0.5 to pH 5, and further preferably pH 0.5 to pH 3.

A surfactant contained in such a washing solution may be any one of nonionic, anionic, and cationic surfactants, for example. A nonionic surfactant is preferable.

Specific examples of a surfactant used in the present invention include polyoxyethylene lauryl ether, polyoxyethylene stearyl ether, polyoxyethylene sorbitan monolaurate (Tween™ 20), polyoxyethylene sorbitan monooleate (Tween™ 80), polyoxyethylene octyl phenyl ether (Triton™ X-100), nonyl phenol ethylene oxide, polyethylene oxide, polyoxyethylene nonyl phenyl ether, polyethylene glycol monostearate, polyoxyethylene sorbitan monopalmitate, glycerin monolaurate, glycerin monopalmitate, glycerin monostearate, glycerin monooleate, pentaerythritol monolaurate, sorbitan monopalmitate, sorbitan behenate, sorbitan distearate, digycerin monooleate, triglycerin dioleate, sodium lauryl sulfate, sodium dodecylbenzenesulfonate, sodium butylnaphthalenesulfonate, cetyl trimethyl ammonium chloride, and basic pyridinium salts such as dodecylamine hydrochloride, lauric acid lauryl amide ethyl phosphate, triethyl cetyl ammonium iodide, oleylaminodiethylamine hydrochloride, or dodecylpyridinium hydrochloride.

A washing solution may be a solution identical to an amplification solution as described below. In such a case, the below-described amplification solution comprises a surfactant.

A washing solution is developed, while washing a label substance that has non-specifically remained during the development. In order to enhance a washing effect, as a washing solution before the development, a solution that does not contain a label substance is used.

Such a washing solution may also comprise a part of the components of an amplification solution. Such an amplification solution comprises a component that contains silver ions and a reducing agent component acting on silver. A solution containing either one of the components may also be used for washing.

(2). Washing Time

The time required for washing is preferably 10 seconds or more to 300 seconds or less. It is considered that a majority of a label substance remaining in a membrane, other than those used in an antigen-antibody reaction, namely, a majority of non-specifically remaining label substances have been washed out when the tip of a washing solution reaches. However, if the washing time is less than 10 seconds, the label substances existing in the background cannot be reduced to a necessary level. On the other hand, if the washing time exceeds 300 seconds, specifically bound label substances are also washed out by such washing, and it leads to a decrease in signal, namely, a decrease in detection sensitivity. Moreover, when the present method is applied to the diagnosis of a infectious disease or the like, in order to reduce secondary infection wherein a patient transmits to another patient in a waiting room, it is desired to make a diagnosis in front of the patient in a consultation room. If a washing operation is carried out for more than 300 seconds, it takes 20 minutes as an entire examination time, and this time is too long to make a diagnosis in front of a patient. From this viewpoint as well, it is not preferable to carry out a washing operation for more than 300 seconds.

The term "washing time" is used herein to mean a time at which a washing solution is being supplied, when a time point at which the washing solution reaches a zone to be washed is defined as initiation of washing.

(3) Flow Rate of Washing Solution

The flow rate of a washing solution to be developed is closely linked to the degree of washing of a label substance remaining in a membrane, other than those used in an antigen-antibody reaction, namely, a non-specifically remaining label substance. The flow rate of such a washing solution is preferably greater than 0.1 μL/min·mm. If the flow rate is less than 0.1 μL/min·mm, a sufficient washing effect cannot be obtained.

The flow rate of a washing solution can be obtained by measuring the water content of a water absorbent pad after a washing operation and converting the measured water content to a flow rate per minute per flow channel width when the width of the water absorbent pad is defined as the width of a flow channel.

The flow rate is determined depending on the material, fiber diameter, density, fiber thickness and surface treatment method of a washing solution addition pad and a water absorbent pad used for the supply of the washing solution, and additives such as a surfactant. In addition, the flow rate is determined also depending on a combination of washing solution addition pads used for the supply of the washing solution, the condition of the washing solution addition pad that overlaps an immunochromatographic strip, and the compression degree of the washing solution addition pad that overlaps the immunochromatographic strip. Using a washing solution addition pad and water absorbent pad that comprise glass fibers, a washing solution can be supplied at a high flow rate.

(4). Development of Washing Solution and Direction Thereof

After a sample solution has been developed, a washing solution is used to wash a label substance remaining on an immunochromatographic strip, other than those bound to the sample via an antigen-antibody reaction. Methods for supplying such a washing solution include: a method of directly adding a washing solution to a sample-dropping portion after a sample solution has been developed; a method comprising previously adhering a washing solution addition pad and a water absorbent pad used for supplying a washing solution to a strip, and then adding the washing solution to the washing solution addition pad, so as to supply the washing solution to the water absorbent pad direction; a method comprising previously preparing a washing solution addition portion on a strip, and then adding a washing solution to the washing solution addition portion after a sample solution has been developed; and a method comprising developing a sample solution on a strip, and then adhering a washing solution addition pad and a water absorbent pad used for supplying the washing solution to the strip.

In the present specification, the term "the developing direction of a solution containing an analyte" is used to mean a direction that connects a sample addition pad and an absorbent pad. The term "the developing direction of a washing solution" is used to mean a direction that connects a washing solution addition pad and water absorbent pad used for supplying a washing solution.

When an angle of 45 to 170 degrees can be made between the developing direction of an analyte and the developing direction of a washing solution, a high washing effect can be obtained. Further, the angle between the developing direction of the analyte and the developing direction of the washing solution is preferably 60 to 170 degrees, and more preferably 60 to 150 degrees.

The type of a washing solution addition pad (which is also referred to as a "second insoluble carrier") is not particularly limited, as long as a washing solution can be added to the pad. Examples of such a washing solution addition pad that can be used herein include a glass fiber pad, a cellulose membrane, and a nitrocellulose membrane.

The type of a water absorbent pad is not particularly limited, as long as it is a substance capable of absorbing water. Examples of such a washing absorbent pad that can be used herein include cellulose, nitrocellulose, a glass fiber, and a mixture thereof.

In general, methods for washing a porous body include a method of washing such a porous body by immersing it in a washing solution and a method of washing such a porous body by supplying a liquid into it. However, liquid displacement does not sufficiently occur in a porous body in the case of such immersion method, and thus this method requires a long time for a washing operation. In contrast, in the case of the method of washing a porous body by supplying a liquid into a membrane, which is applied in the present system, liquid displacement sufficiently occurs, and thus a washing operation can be carried out in a short time. Hence, in the present system, as a result of intensive studies directed towards achieving a method capable of fully washing a label substance non-specifically remaining in a porous body in a short time, the inventors have found a method for developing a washing solution from the aforementioned developing direction and carrying out a washing operation.

(General Explanation of the Present Invention)

An immunochromatography kit and an immunochromatography method of the present invention will be described as follows.

1. Immunochromatography

In general, immunochromatography is a method for determining and/or measuring an analyte, simply, rapidly and specifically, by the following means. That is to say, a chromatographic carrier having at least one reaction zone comprising an immobilizing reagent (an antibody, an antigen, etc.) capable of binding to an analyte is used as an immobilization phase. On this chromatographic carrier, a dispersed liquid formed by dispersion of a labeling substance used in detection, which is modified by a reagent capable of binding to an analytical target, is used as a mobile phase, and the mobile phase is moved in the chromatographic carrier in a chromatographic manner. At the same time, the aforementioned analytical target specifically binds to the labeling substance used in detection, and they reach the aforementioned reaction zone. At the aforementioned reaction zone, a complex of the aforementioned analytical target and the aforementioned labeling substance used in detection specifically binds to the aforementioned immobilizing reagent. Utilizing the phenomenon whereby the labeling substance used in detection is concentrated in the immobilizing reagent portion only when the analytical target exists in an analyzed solution, the presence of a product to be detected in the analyzed solution is qualitatively and quantitatively analyzed by visual observation or using an adequate apparatus.

The apparatus used to perform such an immunochromatography in the present invention may comprise a compound containing silver and a reducing agent for silver ion. A signal is amplified by an amplification reaction using, as a core, a complex of the aforementioned analytical target and the aforementioned labeling substance used in detection binding to the aforementioned immobilizing reagent, so as to achieve high sensitivity. According to the present invention, a rapid and highly sensitive immunochromatography can be carried out.

2. Test Sample

The type of a test sample that can be analyzed by the immunochromatography of the present invention is not particularly limited, as long as it may comprise an analytical target. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

3. Pre-Treatment of Test Sample

In the immunochromatography of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

4. Structure of the Kit

The immunochromatographic kit of the present invention may comprises an immunochromatographic strip for detecting the present or absence of an analyte, an amplification liquid adding pad, and a water absorbent pad. The amplification liquid adding pad and the water absorbent pad may be composed of separate members, or may be an integrated-type member. The immunochromatographic strip, the amplification liquid adding pad, and the water absorbent pad are overlapped and laminated with each other at a membrane portion so that they are adhered to each other. Pressure may be applied, or a tape or an adhesive may be used, but the means for adhesion is not particularly limited.

Figure 6:
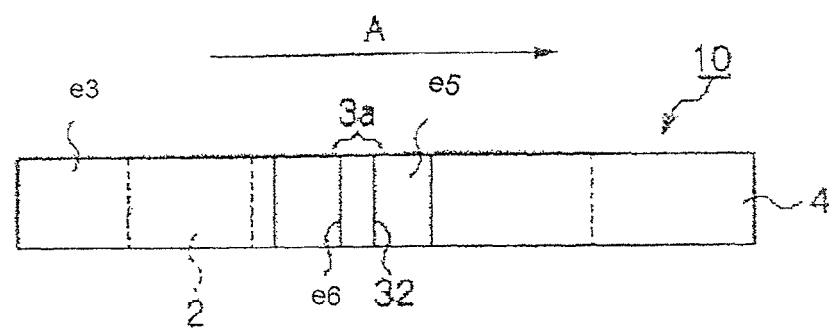
FIG. 6 is a plan view schematically showing an immunochromatographic strip.
Figure 7:
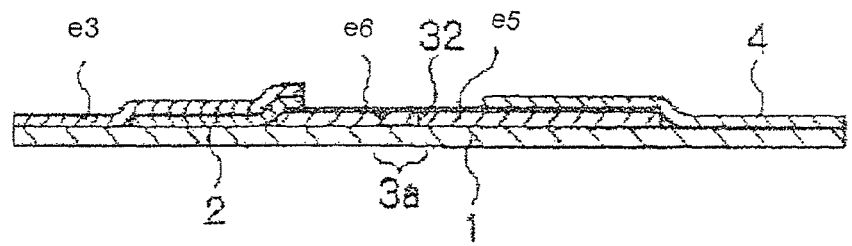
FIG. 7 is a longitudinal sectional view schematically showing a longitudinal section of the immunochromatography kit shown in FIG. 6.

The type of an immunochromatographic strip that can be used in the immunochromatography of the present invention is not particularly limited, as long as it is an immunochromatographic strip that can be used in a common immunochromatography. For example, FIG. 6 schematically shows a longitudinal section of one example of the immunochromatographic strip. FIG. 7 is a longitudinal sectional view schematically showing a longitudinal section of the immunochromatography kit shown in FIG. 6.

In an immunochromatographic strip 10 of the present invention, a sample-adding pad e3, a labeling substance-retaining pad (e.g. a gold colloid antibody-retaining pad) 2, a chromatographic carrier (e.g. an antibody-immobilized membrane) e5, and an absorbent pad 4 are disposed in this order on an adhesive sheet 1 from the upstream to the downstream of a development direction.

The chromatographic carrier e5 has a capturing zone 3a and a detection zone (which is also referred to as a "detection portion") e6 that is a region on which an antibody or an antigen specifically binding to an analytical target is immobilized. The chromatographic carrier e5 also has a control zone (which is also referred to as a "control portion") 32 that is a region on which a control antibody or antigen is immobilized, as desired. Further, the detection zone e6 and the control zone 32 comprise organic silver salts used for amplification and reducing agents used for silver ion.

The labeling substance-retaining pad 2 can be produced by preparing a suspension containing a labeling substance, applying the suspension to a suitable absorbent pad (e.g. a glass fiber pad), and then drying it.

As the sample-adding pad e3, a glass fiber pad can be used, for example.

The strip for developing an amplification liquid has a similar structure with that of the immunochromatographic strip, except that it is prepared without using gold colloid and antibody. However, the structure of the strip for developing an amplification liquid may be more simple, and the structure thereof is not limited to the aforementioned structure.

Figure 11:
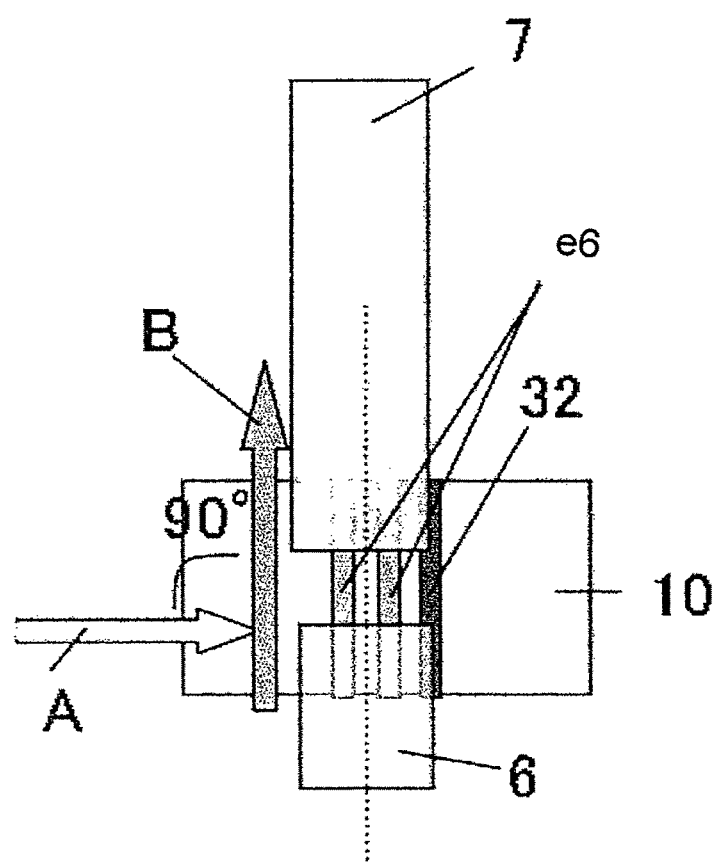
FIG. 11 is a plan view schematically showing an immunochromatography kit for carrying out the washing of the present invention.

FIG. 11 is a plan view schematically showing an immunochromatography kit for carrying out the washing of the present invention. In an immunochromatographic strip 10, an addition portion for washing solution is provides previously or after a test sample solution is developed. If desired, a water absorbent pad for washing solution 7 may be provided. "B" represents the developing direction of washing solution.

4-1. Labeling Substance Used in Detection

As a labeling substance used in detection, a color particle used in immune agglutination can be used. For example, metals such as a metal colloid can be used. The mean particle diameter of a carrier particle (or colloid) is preferably between 0.02 and 10 μm. Liposomes or microcapsules containing pigments can also be -used as such color particles. Conventionally known color metal colloids can all be used as such color particles for labeling. Examples of such color metal colloids include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. The mean particle diameter of a metal colloid is preferably between approximately 1 nm and 500 nm, more preferably between 5 nm and 100 nm.

Such a metal colloid can be bound to a specifically binding substance according to conventionally known methods (e.g. The Journal of Histochemistry and Cytochemistry, Vol. 30, No. 7, pp. 691-696 (1982)). That is to say, a metal colloid is mixed with a specifically binding substance (e.g. an antibody) in a suitable buffer at room temperature for 5 or more minutes. After completion of the reaction, a precipitate obtained by centrifugation is dispersed in a solution containing a dispersant such as polyethylene glycol to obtain a metal colloid-labeled specifically binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.).

The present invention is characterized in that the size of the labeling substance for detection at the time of detection is 1 μm or more and 20 μm or less, and preferably 3 μm or more and 20 μm or less. As a method for changing the size of the substance from the size before detection to the size at the time of detection, an amplification reaction using an a reducing agent can be used.

According to the present invention, in an immunochromatography using, as a labeling substance used in detection, a metal colloid labeling substance, a metallic sulfide labeling substance, a metal alloy labeling substance (hereinafter also referred to as a metallic labeling substance), or a metal-containing polymer particle labeling substance, the signal from the aforementioned metallic labeling substance can be amplified. Specifically, after formation of a complex of the analytical target and the labeling substance used in detection, silver ions supplied from a compound containing silver such as an inorganic silver salt or an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target. Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal. Further, since the amplification reaction in the present invention is extremely rapid, good performance is obtained regardless of the size of meal colloid used for label.

In the immunochromatography of the present invention, a metal colloid labeling substance or a metallic sulfide labeling substance may be used as a labeling substance for labeling an antibody or antigen which specifically binds to an analytical target (an antigen or an antibody), or for labeling a standard compound. The type of such a metal colloid labeling substance or a metallic sulfide labeling substance is not particularly limited, as long as it can be used in an ordinary immunochromatography. Examples of such a metal colloid labeling substance include a platinum colloid, a gold colloid, a palladium colloid, a silver colloid, and a mixture thereof. Examples of such a metallic sulfide labeling substance include sulfides of iron, silver, palladium, lead, copper, cadmium, bismuth, antimony, tin, and mercury. In the immunochromatography of the present invention, one or more selected from these metal colloid labeling substances and/or metallic sulfide labeling substances may be used as a labeling substance(s).

4-2. Binding Substance

In the present invention, a labeling substance is modified with a first binding substance reacting with the analyte. A first binding substance reacting with the analyte is immobilized on a labeling substance. The type of the first binding substance reacting with the analyte may be any substance so long as it has an affinity against the analyte. Examples of the first binding substance may include an antibody against the analyte (antigen), an antigen against the analyte (antibody), or an aptamer against the analyte (protein, low molecular weight compound, or the like), but are not limited thereto.

In the present invention, the porous carrier has (a) a second binding substance reacting with the analyte, or (b) a substance binding with the first binding substance. The type of the second binding substance reacting with the analyte may be any substance so long as it has an affinity against the analyte. Examples of the second binding substance may include an antibody against the analyte (antigen), an antigen against the analyte (antibody), or an aptamer against the analyte (protein, low molecular weight compound, or the like), but are not limited thereto. The second binding substance may be the same as or different from the first binding substance.

Examples of the substance binding with the first binding substance may be the analyte, or a substance having a zone which is recognized by the first binding substance, and may be a substance which is obtained by binding a derivative of the analyte with a protein (for example, BSA).

Preferably, the first binding substance is an antibody, and/or the second binding substance is an antibody.

In the immunochromatography of the present invention, the type of an antibody having specificity for an analytical target is not particularly limited. Examples of an antibody used herein include an antiserum prepared from the serum of an animal immunized with the analytical target, an immunoglobulin fraction purified from the antiserum, a monoclonal antibody obtained by cell fusion using the splenic cells of the animal immunized with the analytical target, and the fragments thereof (for example, F(ab')2, Fab, Fab' or Fv). Such an antibody may be prepared by a common method.

The fragmented antibody can be used regardless of animal species, subclasses, and the like. Examples of antibodies that can be used in the present invention include mouse IgG; mouse IgM, rat IgG; rat IgM, rabbit IgG; rabbit IgM, goat IgG, goat IgM, sheep IgG, and sheep IgM. They can be used as either polyclonal or monoclonal antibodies.

The fragmented antibody is a molecule having at least one antigen-binding site, which is derived from complete type-antibody, such as Fab and F(ab')2. The fragmented antibody can be obtained by enzyme or chemical treatment or using genetic engineering techniques.

4-3. Chromatographic Carrier

The chromatographic carrier (or the first insoluble carrier) is preferably a porous carrier. It is particularly preferably a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like.

Usually, a substance used in detection is immobilized on a part of the chromatographic carrier to form a detection zone. The substance used in detection may be directly immobilized on a part of the chromatographic carrier via a physical or chemical bond. Alternatively, the substance used in detection may be bound physically or chemically to fine particles such as latex particles, and thereafter, the fine particles are immobilized on a part of the chromatographic carrier by trapping them thereon. After immobilization of the substance used in detection on the chromatographic carrier, the chromatographic carrier may preferably be subjected to a treatment for preventing unspecific adsorption, such as a treatment using an inert protein, and it may be then used.

4-4. Sample-Adding Pad

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing unspecific adsorption before use.

4-5. Labeling Substance-Retaining Pad

Examples of a material for the labeling substance-retaining pad include a cellulose filter paper, glass fibers, and a nonwoven fabric. Such a labeling substance-retaining pad is prepared by impregnating the pad with a predetermined amount of the labeling substance used in detection as prepared above and then drying it.

4-6. Absorbent Pad

The absorbent pad is a portion for physically absorbing the added sample as a result of the chromatographic migration and for absorbing and removing an unreacted labeling substance, etc. that is not immobilized on the detection portion of the chromatographic carrier. Examples of a material for the absorbent pad include water-absorbing materials such as a cellulose filter paper, a nonwoven fabric, a cloth or cellulose acetate. The chromatographic speed after the chromatographic leading end of the added sample has reached the absorbing portion varies depending on the material and size of the absorbent material, etc. Thus, a speed adequate for the measurement of the analytical target can be determined by selection of the material and size of the absorbent material.

5. Immunological Test Method

Hereinafter, a sandwich method and a competitive method, which are specific embodiments of the immunochromatography of the present invention, will be described.

(Sandwich Method)

In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled. The second antibody is immobilized on a suitable insoluble thin-membrane support (e.g. a nitrocellulose membrane, a glass fiber membrane, a nylon membrane, a cellulose membrane, etc.), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized primary antibody, the analytical target (antigen) and the secondary antibody, the labeled secondary antibody that has not formed the aforementioned immune complex is removed. Subsequently, a region of the insoluble thin-membrane support, on which the second antibody has been immobilized, may be observed so as to detect or quantify the labeling substance, and detect the presence or absence of the analyte in the test sample or measure the amount of the analyte. Alternatively, a metal ion and a reducing agent are supplied, so that a signal from the labeling substance of the labeled primary antibody that has formed the aforementioned immune complex may be amplified and detected. Otherwise, a metal ion and a reducing agent are added to the labeled primary antibody, and they are simultaneously added to the thin-membrane support, so that a signal from the labeling substance of the labeled secondary antibody that has formed the aforementioned immune complex may be amplified, detected and measured.

(Competitive Method)

In the competitive method, an analytical target can be analyzed by the following procedures, for example, but the procedures are not particularly limited thereto. The competitive method is known as a means for detecting a low molecular weight antigen which can not be assayed in the sandwich method.

First, a primary antibody having specificity for an analytical target (an antigen) has previously been prepared. In addition, the primary antibody has previously been labeled with metal colloid or the like. An analytical target, or a compound which has a site which is similar with that of the analytical target and has a same epitope against the primary antibody as that of the analytical target, both of which can bind to the primary antibody, is immobilized on a suitable insoluble thin-membrane support (e.g. a nitrocellulose membrane, a glass fiber membrane, a nylon membrane, a cellulose membrane, etc.). It is then allowed to come into contact with a test sample (or an extract thereof) that is likely to contain the analytical target (the antigen). If the analytical target does not exist in the test sample, an antigen-antibody reaction occurs on the insoluble support between the labeled primary antibody, and the analytical target, or the compound which has a same epitope against the primary antibody as that of the analytical target, both of which can bind to the primary antibody. If the analytical target exists in the test sample, the analytical target (antigen) binds to the labeled primary antibody, and thus an antigen-antibody reaction on the insoluble support between the labeled primary antibody, and the analytical target, or the compound which has a same epitope against the primary antibody as that of the analytical target, both of which can bind to the primary antibody, is inhibited. Namely, binding by the antigen-antibody reaction does not occur.

After completion of the reaction of the immobilized substance which can bind to the primary antibody and the labeled primary antibody, the labeled primary antibody that has not formed the aforementioned immune complex is removed. Subsequently, the substance which can bind to the primary antibody on the insoluble carrier may be observed so as to detect or quantify the labeling substance, and detect the presence or absence of the analyte in the test sample or measure the amount of the analyte. Also, a metal ion and a reducing agent are supplied to a region of the insoluble thin-membrane support, on which the substance which can bind to the primary antibody has been immobilized, for example, so that a signal from the labeling substance of the labeled primary antibody which formed immune complex may be amplified and detected. Otherwise, a metal ion and a reducing agent are added to the labeled primary antibody, and they are simultaneously added to the thin-membrane support, so that a signal from the labeling substance of the labeled secondary antibody that has formed the aforementioned immune complex may be amplified, detected and measured.

6. Amplification Solution

An amplification solution that can be used in the present invention is what is called a developing solution as described in publications common in the field of photographic chemistry (e.g. "Kaitei Shashin kagaku no kiso, Ginen shashin hen (Revised Basic Photographic Engineering, silver salt photography)," (the Society of Photographic Science and Technology of Japan, Colona Publishing Co., Ltd.); "Shashin no kagaku (Photographic Chemistry)," (Akira Sasaki, Shashin Kogyo Shuppan); "Saishin Shoho Handbook (Latest Formulation Handbook)," (Shinichi Kikuchi et al., Amiko Shuppan); etc.).

In the present invention, any type of amplification solution can be used, as long as it is what is called a physical developing solution, which comprises silver ions, and such silver ions in the solution act as a core of development and reduction is carried out using a metal colloid as a center.

7. Compound that Contains Silver

The silver-containing compound used in the present invention may be an organic silver salt, an inorganic silver salt, or a silver complex.

The organic silver salt used in the present invention is an organic compound containing a reducible silver ion. Any one of an organic silver salt, an inorganic silver salt and a silver complex may be used as a compound containing a reducible silver ion in the present invention. For example, a silver nitrate, a silver acetate, a silver lactate, a silver butyrate, etc. have been known.

In addition, such a compound may be a silver salt or a coordination compound that forms a metallic silver relatively stable for light, when it is heated to 50° C. in the presence of a reducing agent.

The organic silver salt used in the present invention may be a compound selected from the silver salts of an azole compound and the silver salts of a mercapto compound. Such an azole compound is preferably a nitrogen-containing heterocyclic compound, and more preferably a triazole compound and a tetrazole compound. The mercapto compound is a compound having at least one mercapto group or thione group in the molecule thereof.

The silver salt of the nitrogen-containing heterocyclic compound of the present invention is preferably the silver salt of a compound having an imino group. Typical compounds include, but are not limited to, the silver salt of 1,2,4-triazole, the silver salt of benzotriazole or a derivative thereof (for example, a methylbenzotriazole silver salt and a 5-chlorobenzotriazole silver salt), a 1H-tetrazole compound such as phenylmercaptotetrazole described in U.S. Pat. No. 4,220,709, and imidazole or an imidazole derivative described in U.S. Pat. No. 4,260,677. Among these types of silver salts, a benzotriazole derivative silver salt or a mixture of two or more silver salts is particularly preferable.

The silver salt of the nitrogen-containing heterocyclic compound used in the present invention is most preferably the silver salt of a benzotrialzole derivative.

The compound having a mercapto group or a thione group of the present invention is preferably a heterocyclic compound having 5 or 6 atoms. In this case, at least one atom in the ring is a nitrogen atom, and other atoms are carbon, oxygen, or sulfur atoms. Examples of such a heterocyclic compound include triazoles, oxazoles, thiazoles, thiazolines, imidazoles, diazoles, pyridines, and triazines. However, examples are not limited thereto.

Typical examples of the silver salt of the compound having a mercapto group or a thione group include, but are not limited to, the silver salt of 3-mercapto-4-phenyl-1,2,4-triazole, the silver salt of 2-mercapto-benzimidazole, the silver salt of 2-mercapto-5-aminothiazole, the silver salt of mercaptotriazine, the silver salt of 2-mercaptobenzoxazole, and the silver salt of compounds described in U.S. Pat. No. 4,123,274.

As such a compound having a mercapto group or a thione group of the present invention, a compound that does not contain a hetero ring may also be used. As such a mercapto or thione derivative that does not contain a hetero ring, an aliphatic or aromatic hydrocarbon compound having total 10 or more carbon atoms is preferable.

Among such mercapto or thione derivatives that do no contain a hetero ring, useful compounds include, but are not limited to, the silver salt of thioglycolic acid (for example, the silver salt of S-alkylthioglycolic acid having an alkyl group containing 12 to 22 carbon atoms) and the silver salt of dithiocarboxylic acid (for example, the silver salt of dithioacetic acid and the silver salt of thioamide).

An organic compound having the silver salt of carboxylic acid is also preferably used. It is straight-chain carboxylic acid, for example. Specifically, carboxylic acid containing 6 to 22 carbon atoms is preferably used. In addition, the silver salt of aromatic carboxylic acid is also preferable. Examples of such aromatic carboxylic acid and other carboxylic acids include, but are not limited to, substituted or unsubstituted silver benzoate (for example, silver 3,5-dihydroxybenzoate, silver o-methylbenzoate, silver m-methylbenzoate, silver p-methylbenzoate, silver 2,4-dichlorobenzoate, silver acetamide benzoate and silver p-phenylbenzoate), silver tannate, silver phthalate, silver terephthalate, silver salicylate, silver phenylacetate, and silver pyromellitate.

In the present invention, aliphatic acid silver containing a thioether group as described in U.S. Pat. No. 3,330,663 can also be preferably used. A soluble silver carboxylate having a hydrocarbon chain containing an ether bond or a thioether bond, or a soluble silver carboxylate having a sterically hindered substituent on an α-position (of the hydrocarbon group) or an ortho-position (of the aromatic group) can also be used. These silver carboxylates have an improved solubility in a coating solvent, which provides a coating material having little light scattering.

Such silver carboxylates are described in U.S. Pat. No. 5,491,059. All of the mixtures of the silver salts described therein can be used in the invention, as necessary.

The silver salt of sulfonate as described in U.S. Pat. No. 4,504,575 can also be used in the embodiment of the present invention.

Further, for example, the silver salt of acetylene described in U.S. Pat. Nos. 4,761,361 and 4,775,613 can also be used in the present invention. It can be provided as a core-shell type silver salt as described in U.S. Pat. No. 6,355,408. Such silver salt is composed of a core consisting of one or more silver salts and a shell consisting of one or more different silver salts.

In the present invention, another product useful as a non-photosensitive silver source is a silver dimer composite consisting of two different types of silver salts described in U.S. Pat. No. 6,472,131. Such a non-photosensitive silver dimer composite consists of two different types of silver salts. When the aforementioned two types of silver salts include a linear saturated hydrocarbon group as a silver ligand, a difference in the numbers of carbon atoms of the ligands is 6 or greater.

The organic silver salt is contained as silver generally in an amount of 0.001 to 0.2 mol/m$^2$, and preferably 0.01 to 0.05 mol/m$^2$, in terms of the silver amount.

The inorganic silver salt or the silver complex used in the present invention is a compound containing a reducible silver ion. Preferably, such an inorganic silver salt or a silver complex is an inorganic silver salt or a silver complex, which forms metallic silver relatively stable for light, when the salt or complex is heated to 50° C. or higher in the presence of a reducing agent.

Examples of the inorganic silver salt used in the present invention include: a silver halide (such as silver chloride, silver bromide, silver chlorobromide, silver iodide, silver chloroiodide, silver chloroiodobromide, and silver iodobromide); the silver salt of a silver thiosulfate (e.g. a sodium salt, a potassium salt, an ammonium salt, etc.); the silver salt of a silver thiocyanate (e.g. a sodium salt, a potassium salt, an ammonium salt, etc.); and the silver salt of a silver sulfite (e.g. a sodium salt, a potassium salt, an ammonium salt, etc.).

The inorganic silver salt used in the present invention is preferably a silver halide or silver nitrate.

A method for forming the particles of the silver halide used in the invention is well known in the photographic industry. For example, methods described in Research Disclosure No. 17029, June 1978, and U.S. Pat. No. 3,700,458 may be used. Specifically, such a silver halide may be prepared by adding a silver-supplying compound (for example, a silver nitrate) and a halogen-supplying compound to a solution of a gelatin or other polymers.

The particle size of the silver halide is preferably very small in order to reduce examination noise. Specifically, the size is preferably 0.20 μm or less, more preferably 0.10 μm or less, and even more preferably in the range of nanoparticles. The term "particle size" is used herein to mean a diameter of a circular image having the same area as the projected area of the silver halide particle (the projected area of the main plane in the case of a tabular particle).

A silver thiosulfate, a silver thiocyanate, and a silver sulfite can also be prepared in the same manner as the formation of silver halide particles, by mixing a silver-supplying compound (such as a silver nitrate) with a thiosulfate (e.g. a sodium salt, a potassium salt, an ammonium salt, etc.), a thiocyanate (e.g. a sodium salt, a potassium salt, an ammonium salt, etc.), and a sulfite (e.g. a sodium salt, a potassium salt, an ammonium salt, etc.), respectively.

In general, if the concentration of silver ion in the amplification solution is too high, such silver ion is reduced in the amplification solution. In order to prevent such a phenomenon, a complexing agent may be used to cause the silver ion to form a complex. As such a complexing agent, amino acids such as glycine and histidine, heterocyclic bases, imidazole, benzimidazole, pyrazole, purine, pyridine, aminopyridine, nicotinamide, quinoline, and other similar aromatic heterocyclic compounds have been known. These compounds are described in E.P. Patent No. 0293947, for example. Further, as a complex salt-forming agent, thiosulfate, thiocyanate, and the like can also be used. Specific examples of the silver complex used in the present invention include a complex of a thiosulfate and a silver ion, a complex of a thiocyanate and a silver ion, a composite silver complex thereof, a complex of a sugar thione derivative and a silver ion, a complex of a cyclic imide compound (e.g. uracil, urazole, 5-methyluracil, barbituric acid, etc.) and a silver ion, and a complex of a 1,1-bissulfonylalkane and a silver ion. A preferred silver complex used in the invention is a complex of a cyclic imide compound (e.g. uracil, urazole, 5-methyluracil, barbituric acid, etc.) and a silver ion.

The silver complex used in the present invention may be prepared by a generally-known salt forming reaction. For example, the silver complex may be prepared by mixing in water or a water-miscible solvent a water-soluble silver supplier (such as a silver nitrate) with a ligand compound corresponding to the silver complex. The prepared silver complex can be used, after salts generated as by-products have been removed by a known desalting method such as dialysis or ultrafiltration.

The inorganic silver salt or the silver complex is contained as silver generally in an amount of 0.001 to 0.2 mol/m$^2$, and preferably 0.01 to 0.05 mol/m$^2$, in terms of the silver amount.

When an inorganic silver salt or a silver complex is used, a solvent for them is preferably used. The solvent used in the present invention is preferably a compound used as a ligand for forming a silver complex described in the above paragraphs for the "silver complex." Examples of such a compound used as a solvent in the present invention include a thiosulfate, a thiocyanate, a sugar thione derivative, a cyclic imide compound, and a 1,1-bissulfonylalkane. The solvent used in the present invention is more preferably a cyclic imide compound such as uracil, urazole, 5-methyluracil, or barbituric acid. The solvent used in the present invention is preferably used at a molar ratio of 0.1 to 10 moles with respect to silver ions.

8. Reducing Agent Used for Silver Ion

As a reducing agent used for silver ion, either inorganic or organic materials capable of reducing silver(I) ion to silver, or the mixtures thereof, may be used.

As an inorganic reducing agent, reducible metal salts and reducible metal complex salts whose valence can be changed with metal ions such as $Fe^{2+}$, $V^{2+}$ or $Ti^{3+}$ have been known. These salts can be used in the present invention. When such an inorganic reducing agent is used, it is necessary to form a complex with the oxidized ion or reduce it, so as to remove or detoxify the oxidized ion. For example, in a system using $Fe^{+2}$ as a reducing agent, citric acid or EDTA is used to form a complex with $Fe^{3+}$ as an oxide, so as to detoxify it.

In the present system, such an inorganic reducing agent is preferably used. The metal salt of $Fe^{2+}$ is more preferable.

Developing agents used for wet-process silver halide photographic-sensitized materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), or other materials known to those skilled in the art (see, for example, U.S. Pat. No. 6,020,117 (Bauer et al.)) may be used in the present invention.

The term "ascorbic acid reducing agent" means a complex of ascorbic acid and a derivative thereof. Ascorbic acid reducing agents are described in many publications, as described below, including, for example, U.S. Pat. No. 5,236,816 (Purol et al.) and publications cited therein.

The reducing agent used in the present invention is preferably an ascorbic acid reducing agent. Useful ascorbic acid reducing agents include ascorbic acid, an analogue thereof, an isomer thereof, and a derivative thereof. Examples of such compounds include the following compounds. However, examples are not limited thereto.

Examples of such compounds include D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the art), and endiol-type ascorbic acid, enaminol-type ascorbic acid and thioenol-type ascorbic acid such as compounds described in U.S. Pat. No. 5,498,511, EP-A-0585,792, EP-A 0573700, EP-A 0588408, U.S. Pat. Nos. 5,089,819, 5,278,035, 5,384,232 and 5,376,510, JP 7-56286, U.S. Pat. No. 2,688,549, and Research Disclosure 37152 (March, 1995).

Among these compounds, D-, L-, and D,L-ascorbic acid (and an alkali metal salt thereof), and isoascorbic acid (and an alkali metal salt thereof) are preferable. Moreover, a sodium salt is a preferred salt thereof. If necessary, a mixture of these reducing agents may also be used.

A hindered phenol may be preferably used singly or in combination with one or more gradation-hardening reducing agents and/or contrast enhancers.

A hindered phenol is a compound having only one hydroxyl group on a benzene ring and also having at least one substituent at the ortho-position relative to the hydroxyl group. The hindered phenol reducing agent may have plural hydroxyl groups, as long as the hydroxyl groups are located on different benzene rings.

Examples of the hindered phenol reducing agent include binaphthols (that is, dihydroxybinaphthols), biphenols (that is, dihydroxybiphenols), bis(hydroxynaphthyl)methanes, bis(hydroxyphenyl)methanes (that is, bisphenols), hindered phenols, and hindered naphthols, each of which may be substituted.

Typical binaphthols include, but are not limited to, 1,1'-bi-2-naphthol, 1,1'-bi-4-methyl-2-naphthol, and compounds described in U.S. Pat. Nos. 3,094,417 and 5,262,295.

Typical biphenols include, but are not limited to, 2-(2-hydroxy-3-t-butyl-5-methylphenyl)-4-methyl-6-n-hexylphenol, 4,4'-dihydroxy-3,3',5,5'-tetra-t-butylbiphenyl, 4,4'-dihydroxy-3,3',5,5'-tetramethylbiphenyl, and compounds described in U.S. Pat. No. 5,262,295.

Typical bis(hydroxynaphthyl)methanes include, but are not limited to, 4,4'-methylenebis(2-methyl-1-naphthol) and compounds described in U.S. Pat. No. 5,262,295.

Typical bis(hydroxyphenyl)methanes include, but are not limited to, bis(2-hydroxy-3-t-butyl-5-methylphenyl)methane (CAO-5), 1,1'-bis(2-hydroxy-3,5-dimethylphenyl)-3,5,5-trimethyl hexane (NONOX or PERMANAX WSO), 1,1'-bis(3,5-di-t-butyl-4-hydroxyphenyl)methane, 2,2'-bis(4-hydroxy-3-methylphenyl) propane, 4,4'-ethylidene-bis(2-t-butyl-6-methylphenol), 2,2'-isobutylidene-bis(4,6-dimethylphenol) (LOWINOX 221B46), 2,2'-bis(3,5-dimethyl-4-hydroxyphenyl)propane, and compounds described in U.S. Pat. No. 5,262,295.

Typical hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol, and 2-t-butyl-6-methylphenol.

Typical hindered naphthols include, but are not limited to, 1-naphthol, 4-methyl-1-naphthol, 4-methoxy-1-naphthol, 4-chloro-1-naphthol, 2-methyl-1-naphthol, and compounds described in U.S. Pat. No. 5,262,295.

Moreover, other compounds disclosed as reducing agents include amidoximes (for example, phenylamidoxime), 2-thienylamidoxime, p-phenoxyphenylamidoxime, a combination of an aliphatic carboxylic allyl hydrazide and ascorbic acid (for example, a combination of 2,2'-bis(hydroxymethyl)-propionyl-β-phenyl hydrazide and ascorbic acid), a combination of a polyhydroxybenzene and at least one of hydroxylamine, reductone and hydrazine (for example, a combination of hydroquinone and bis(ethoxyethyl)hydroxylamine), piperidi-4-methylphenylhydrazine, hydroxamic acids (for example, phenylhydroxamic acid, p-hydroxyphenylhydroxamic acid, and o-alaninehydroxamic acid), a combination of an azine and a sulfonamidophenol (for example, a combination of phenothiazine and 2,6-dichloro-4-benzenesulfonamidophenol), α-cyanophenylacetic acid derivatives (for example, ethyl-α-cyano-2-methylphenylacetic acid and ethyl-α-cyanophenylacetic acid), bis-o-naphthol (for example, 2,2'-dihydroxy-1-binaphthyl, 6,6'-dibromo-2,2'-dihydroxy-1,1'-binaphthyl, and bis(2-hydroxy-1-naphthyl) methane), a combination of bis-naphthol and a 1,3-dihydroxybenzene derivative (for example, 2,4-dihydroxybenzophenone and 2,4-dihydroxyacetophenone), 5-pyrazolones (for example, 3-methyl-1-phenyl-5-pyrazolone), reductones (for example, dimethylaminohexose reductone, anhydrodihydro-aminohexose reductone, and anhydrodihydro-piperidone-hexose reductone), indane-1,3-diones (for example, 2-phenylindane-1,3-dione), chromans (for example, 2,2-dimethyl-7-t-butyl-6-hydroxychroman), 1,4-dihydroxypyridines (for example, 2,6-dimethoxy-3,5-dicarbetoxy-1,4-dihydropyridine), ascorbic acid derivatives (1-ascorbic palmitate, ascorbic stearate), unsaturated aldehydes (ketones), and 3-pyrazolidones.

Examples of a reducing agent that can be used in the present invention include substituted hydrazines such as sulfonyl hydrazines described in U.S. Pat. No. 5,464,738. Other useful reducing agents are described, for example, in U.S. Pat. Nos. 3,074,809, 3,094,417, 3,080,254 and 3,887,417. Auxiliary reducing agents descried in U.S. Pat. No. 5,981,151 are also useful.

The reducing agent may be a combination of a hindered phenol reducing agent and a compound selected from various auxiliary reducing agents such as those mentioned below. In addition, a mixture of such a combined agent plus a contrast enhancer (that is, a mixture of the 3 components) is also useful. As such an auxiliary reducing agent, it is possible to use trityl hydrazide and formyl-phenyl hydrazide described in U.S. Pat. No. 5,496,695.

A contrast enhancer may be used in combination with the reducing agent. Useful contrast enhancers include, but are not limited to, hydroxylamines (including hydroxylamine and alkyl- and aryl-substituted derivatives thereof), alkanolamines and phthalic ammonium described in U.S. Pat. No. 5,545,505, hydroxamic acid compounds described in U.S. Pat. No. 5,545,507, N-acylhydrazine compounds described in U.S. Pat. No. 5,558,983, and hydrogen atom donor compounds described in U.S. Pat. No. 5,637,449.

Not all combinations of reducing agents and organic silver salts are equally effective. A preferred combination is a benzotriazole silver salt used as an organic silver salt, a substituted compound thereof or a mixture thereof, with an ascorbic acid reducing agent used as a reducing agent.

The reducing agent of the present invention may be contained in an amount of 1 mass % to 10 mass % (dry mass) based on the amount of silver in organic silver. When the reducing agent is added to a layer other than the layer containing the organic silver salt in a multilayer structure, the amount of the reducing agent is slightly higher, and it is desirably from approximately 2 mass % to approximately 15 mass %. An auxiliary reducing agent is contained in an amount of about 0.001 mass % to 1.5 mass % (dry weight).

9. Other Auxiliary Agents

Other auxiliary agents contained in the amplification solution may include a buffer, an antiseptic such as an antioxidant or an organic stabilizer, and a speed regulator. Examples of a buffer used herein include buffers comprising acetic acid, citric acid, sodium hydroxide, a salt thereof, or tris(hydroxymethyl)aminomethane, and other buffers used in ordinary chemical experiments. Using these buffers as appropriate, the pH of the amplification solution can be adjusted to the optimal pH.

10. Method for Calculation of an Average Particle Size at the Time of Detection

At the time of detection (after amplification), a test line is cut out, and The rear surface of a sample was applied to a sample support using a carbon paste and then subjected to carbon coating. The shape and the size are observed by a scanning electron microscope (SEM). For example, the surfaces of samples are observed under SEM (specifically, under FE-STEM S-5500 (manufactured by Hitachi High-Technologies Corporation)) using acceleration voltage of 10 KV and reflected electrons. Subsequently, 100 signal particles are selected, and the circle-equivalent diameter of projected area of particles are measured. Then, the average particle size is calculated and is defined as the average particle size at the time of detection.

The present invention will be more specifically described in the following examples. However, these examples are not intended to limit the scope of the present invention.

EXAMPLES

Example A (1) Preparation of Immunochromatography Kit for Detection of Influenza Types A and B
(1-1) Preparation of Anti-Influenza Types A and B Antibodies-Modified (Immobilized) Gold Colloids
(1-1-1) Preparation of Anti-Influenza Type A Antibody-Modified (Immobilized) Gold Colloid 1 mL of a 90 μg/mL anti-influenza type A monoclonal antibody (Anti-Influenza A SPTN-5 7307, Medix Biochemica) solution was added to a gold colloidal solution having pH adjusted by addition of 1 mL of a 50 mM $KH_2PO_4$ buffer (pH 7.5) to 9 mL of a 50-nm diameter gold colloidal solution (EM.GC50, BBI), followed by agitation. The mixture was allowed to stand for 10 minutes and then 550 μL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified (immobilized) gold colloid (50 nm) solution was obtained.

(1-1-2) Preparation of Anti-Influenza Type B Antibody-Modified (Immobilized) Gold Colloid 1 mL of a 80 μg/mL anti-influenza type B monoclonal antibody (MONOTOPE aby Influenza B Virus (nuclear) Purified 1131, ViroStat, Inc.) solution was added to a gold colloidal solution having pH adjusted by addition of 1 mL of a 50 mM $KH_2PO_4$ buffer (pH 8.0) to 9 mL of a 50-nm diameter gold colloidal solution (EM.GC50, BBI), followed by agitation. The mixture was allowed to stand for 10 minutes and then 550 μL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified (immobilized) gold colloid (50 nm) solution was obtained.

(1-2) Preparation of Gold Colloidal Antibody-Holding Pad

The influenza type A and B antibodies-modified (immobilized) gold colloids prepared in (1-1) above were mixed at an OD ratio of 1:1, and the mixture was then diluted with water and a coating solution for a gold colloid (20 mM Tris-Hcl buffer (pH 8.2), 0.05% PEG (Mw: 20000), and 5% sucrose) to set the OD at 520 nm to 3.0. This solution was uniformly applied to glass fiber pads (Glass Fiber Conjugate Pad, Millipore) cut to a size of 8 mm×150 mm in an amount of 0.8 mL per pad. The pads were dried under reduced pressure overnight to obtain gold colloidal antibody-holding pads.

(1-3) Preparation of Antibody-Immobilized Membrane (Chromatographic Carrier)

An antibody-immobilized membrane was prepared in the following manner by immobilizing an antibody on a nitrocellulose membrane (HiFlow Plus HF120 with a plastic lining; Millipore) cut to a size of 25 mm×200 mm. The membrane, with one of its long sides facing downward, was coated with an anti-influenza type A monoclonal antibody for immobilization (Anti-Influenza A SPTN-5 7307, Medix Biochemica) solution prepared at a concentration of 1.5 mg/ml with the use of a coater of inkjet type (BioDot Ltd.). Specifically, the membrane was coated so that a linear portion thereof 7 mm above the lower edge was coated to have a width of approximately 0.7 mm. Likewise, the membrane was coated with an anti-influenza type B monoclonal antibody for immobilization (MONOTOPE aby Influenza B Virus (nuclear) Purified 1131, ViroStat, Inc.) solution prepared at a concentration of 1.5 mg/ml with the use of a coater of inkjet type (BioDot Ltd.). Specifically, the membrane was coated so that a linear portion thereof 10 mm above the lower edge was coated to have a width of approximately 0.7 mm. In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 13 mm above the lower edge was coated. The coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, and 50 mM Tris-HCl (pH 7.5) buffer) in a similar vat and then allowed to stand therein for 30 minutes. The membrane was removed from the solution and then dried overnight at room temperature to give an antibody-immobilized membrane.

(1-4) Preparation of Immunochromatography Strip

The antibody-immobilized membrane prepared in (1-3) above was adhered to a back pressure-sensitive adhesive sheet 1 (ARcare9020, NIPPN TechnoCluster, Inc.). At this time, the membrane was used with the anti-influenza type A antibody line side (one of the long sides of the membrane) facing downward. The gold colloidal antibody-holding pad prepared in 2 above was adhered onto the antibody-immobilized membrane such that the pad overlapped the lower portion of the antibody-immobilized membrane by approximately 2 mm. The sample addition pad (glass fiber pad (Glass Fiber Conjugate Pad, Millipore) cut to a size of 18 mm×150 mm) was adhered to the gold colloidal antibody-holding pad such that the sample addition pad overlapped the lower portion of the gold colloidal antibody-holding pad by approximately 4 mm. An absorbent pad (cellulose glass membrane cut to a size of 20 mm×150 mm (CF6, Whatman)) was adhered onto the antibody-immobilized membrane such that the absorbent pad overlapped the upper portion of the antibody-immobilized membrane by approximately 5 mm. With the use of a guillotine cutter (CM4000, NIPPN TechnoCluster, Inc.), the thus overlapped and adhered members (members that constitute a main body of the immunochromatography body member) were cut in parallel to the short sides of the overlapped members at 15-mm intervals, whereby 15 mm×55 mm immunochromatographic strips were prepared. An immunochromatography kit for testing was prepared with these strips. The volume of the absorbent pad was 240 $mm^3$.

(1-5) Preparation of Immunochromatography Kit Used in Amplification from Different Directions A straight line that connected an amplification solution addition pad and a water absorbent pad was allowed to pass a point located in the center from both ends of a strip in an area between the two capturing portions (TL) of the immunochromatography kit used in tests prepared in (1-4) above, so that the angle between the developing direction of the amplification solution and the developing direction of the sample solution was set at 45, 60, 90, 135, 150 and 170 degrees. An amplification solution addition pad (glass fiber pad (Glass Fiber Conjugate Pad, Millipore) cut to a size of 18 mm×8 mm), to which a back adhesive sheet with a size of 13 mm×8 mm (ARcare 9020; NIPPN TechnoCluster, Inc.) had been adhered, was attached with a tape to the upstream tip of the developed washing solution, whereas a water absorbent pad (cellulose membrane (CF6; Whatman; thickness: 1.37 mm; volume: 1096 $mm^3$) cut to a size of 100 mm×8 mm), to which a back adhesive sheet with a size of 95 mm×8 mm (ARcare 9020; NIPPN TechnoCluster, Inc.) had been adhered, was attached with a tape to the downstream tip thereof.

(1-6) Washing Solution

A 1% BSA-containing PBS buffer prepared by dissolving 1% by weight of BSA (Sigma) in a PBS buffer (Wako Pure Chemical Industries, Ltd.) was used as a washing solution.

(1-7) Preparation of Silver Amplification Solution
(1-7-1) Preparation of Amplification Solution A
(1-7-1-1) Preparation of Amplification Solution A-1

40 mL of a 1 mol/L iron nitrate aqueous solution produced by dissolving iron (III) nitrate nonahydrate (Wako Pure Chemical Industries, Ltd.; 095-00995) in water, 10.5 g of citric acid (Wako Pure Chemical Industries, Ltd.; 038-06925), 0.1 g of dodecylamine (Wako Pure Chemical Industries, Ltd.; 123-00246), and 0.44 g of a surfactant, $C_9H_{19}$—$C_6H_4$—O—$(CH_2CH_2O)_{50}$H were dissolved in 325 g of water. After all the aforementioned components had been dissolved in the water, 40 mL of nitric acid (10% by weight) was added to the mixed solution, while stirring with a stirrer. Thereafter, 80 mL of the solution was weighed, and 11.76 g of iron (II) ammonium sulfate hexahydrate (Wako Pure Chemical Industries, Ltd.; 091-00855) was added thereto. The obtained mixture was defined as amplification solution A-1.

(1-7-1-2) Preparation of Amplification Solution A-2

Water was added to 10 mL of a silver nitrate solution (containing 10 g of silver nitrate), resulting in a total amount of 100 g. This solution was defined as amplification solution A-2 (10% by weight of silver nitrate aqueous solution).

(1-7-1-3) Preparation of Amplification Solution A 40 mL of amplification solution A-1 was weighed, and 4.25 mL of amplification solution A-2 was then added thereto, followed by stirring. The obtained mixture was defined as amplification solution A.

(2) Evaluation

Comparative Example 1

Amplification from 0-Degree Direction (2-1) Addition and Development of Antigen Solution A quick S-influ A·B "Seiken" negative/positive control (product No. 322968; DENKA SEIKEN Co., Ltd.) was used as a sample solution. This positive control solution was diluted with a PBS buffer containing 1% by mass of BSA. The detection limit of both type A and B was 1/40, when a commercially available immunochromatography kit "Capillia Flu A+B" (Alfresa Pharma Corp.) was used. This time, this positive control was diluted to 1/200 with a PBS buffer containing 1% by mass of BSA, and the obtained solution was used as a sample solution.

300 μL of the sample solution was added dropwise to the sample addition pad of the immunochromatography kit used for tests, which had been prepared in (1-4) above, such that the sample solution could be uniformly applied on the pad. Thereafter, it was left at rest for 10 minutes. This time, the applied concentration was less than the detection limit concentration (1/40 diluted solution even in the case of the present kit), and thus a detection line could not be confirmed by visual observation.

A PBS buffer was supplied to this membrane so as to wash the background. Thereafter, a detection line portion was cut out, and gold was then extracted with aqua regia. Subsequently, a High Resolution ICP Mass Spectrometer, HR-ICP-MS, (Element XR; Thermo Fisher Scientific K.K.) was used to quantify the amount of gold. By setting the particle diameter of a gold colloid at 50 nm, the measured gold amount was converted to the number of gold colloids. As a result, the number of gold colloids was found to be 870,000 particles/$mm^3$ (the mean value of 3 times of measurements).

In the present experiment, the height of a liquid face that depended on the form of a washing solution container during the washing operation, the form and material of the sample addition pad of an immunochromatography kit, an experimental environment (temperature and humidity), the material and thickness of the absorbent pad, connection of the absorbent pad with a nitrocellulose membrane, and the like are factors for changing a water-absorbing speed and the amount of the washing solution absorbed. Thus, it is necessary to keep these factors constant in the experiment. The water-absorbing speed and the amount of the washing solution absorbed are factors for determining the final washing effect (a decrease in the remaining amount of gold fine particles). This experiment was carried out at an air temperature of 22±3 C.° and a humidity of 50±15%.

(2-2) Signal Amplification with Amplification Solution and Background Evaluation After completion of the development of the antigen solution, all pads were removed from the immunochromatographic stip. An amplification solution addition pad (glass fiber pad (Glass Fiber Conjugate Pad, Millipore) cut to a size of 18 mm×8 mm), to which a back adhesive sheet with a size of 13 mm×8 mm (ARcare 9020; NIPPN TechnoCluster, Inc.) had been adhered, was attached with a tape to the upstream tip of the developed washing solution, whereas a water absorbent pad (cellulose membrane (CF6; Whatman) cut to a size of 100 mm×8 mm), to which a back adhesive sheet with a size of 95 mm×8 mm (ARcare 9020; NIPPN TechnoCluster, Inc.) had been adhered, was attached with a tape to the downstream tip thereof. The amplification addition pad was immersed in a plastic tray containing 40 mL of amplification solution A prepared in (1-6) above. While stirring with a stirrer, silver amplification was carried out for 2 minutes. Thereafter, this membrane was removed from the amplification solution, and it was then well washed with water for 3 minutes. Thereafter, the membrane was subjected to measurement using a concentration measurement apparatus for immunochromatography (ICA-1000; Hamamatsu Photonics K.K.) so as to measure an optical concentration reflecting to a reference white board. This measurement was carried out twice, and the average value was then rounded off to the fourth decimal place. The obtained value was defined as a background measurement result. As a measurement position, a point located in the center from both ends of a membrane in an area between the two capturing portions (TL) of the membrane was measured. The thus obtained concentraions were defined as background concentrations, and they are shown in FIG. 15.

Moreover, the concentration of a membrane after amplification, to which no gold colloids had been supplied, and the concentration of a membrane after amplification, on which no washing operations had been performed in (2-1) above are also shown in the table. A value obtained by subtracting this value from each measured background concentration was considered to be background caused by background gold due to remaining gold, and it is also shown in FIG. 3.

(2-3) Evaluation of Ease of Seeing Line

The ease of seeing a detection line amplified in (2-2) above was evaluated using the symbols ⊚, ○, Δ, × and ×× (invisible) in the order that the contrast of the detection line to the background was clear and thus that the line was easily seen. The results are shown in FIG.15.

Example A-1

Amplification from 30-Degree Direction

The kit prepared in (1-5) above was used such that the angle between the developing direction of the amplification solution and the developing direction of the sample solution became 30 degrees. Addition of an antigen solution was carried out in the same manner as that described in (2-1) above. Ten minutes after the addition of the antigen solution, the amplification solution addition pad was immersed in a plastic tray containing 40 mL of the amplification solution A prepared in (1-6) above, and silver amplification was then carried out for 2 minutes. Thereafter, this membrane was removed from the amplification solution, and it was then well washed with water for 3 minutes. Thereafter, the membrane was subjected to measurement using a concentration measurement apparatus for immunochromatography (ICA-1000; Hamamatsu Photonics K.K.) so as to measure an optical concentration reflecting to a reference white board. This measurement was carried out twice, and the average value was then rounded off to the fourth decimal place. The obtained value was defined as a background measurement result. As a measurement position, a point located in the center of two capturing portions (TL) that is the center from both ends of the membrane in an area between the two capturing portions (TL) of the membrane was measured. The thus obtained concentrations were defined as background concentrations, and they are shown in FIG. 15.

Moreover, the concentration of a membrane after amplification, to which no gold colloids had been supplied, and the concentration of a membrane after amplification, on which no washing operations had been performed in (2-1) above are also shown in the table. A value obtained by subtracting this value from each measured background concentration was considered to be background caused by background gold due to remaining gold, and it is also shown in FIG. 15. Thereafter, the experiment was carried out in the same manner as (2-3) above.

Example A-2

Amplification from 45-Degree Direction

The kit prepared in (1-5) above was used such that the angle between the developing direction of the amplification solution and the developing direction of the sample solution became 45 degrees. Except for this, the experiment was carried out in the same manner as that described in <Example A-1>.

Example A-3

Amplification from 60-Degree Direction

The kit prepared in (1-5) above was used such that the angle between the developing direction of the amplification solution and the developing direction of the sample solution became 60 degrees. Except for this, the experiment was carried out in the same manner as that described in <Example A-1>.

Example A-4

Amplification from 90-Degree Direction

The kit prepared in (1-5) above was used such that the angle between the developing direction of the amplification solution and the developing direction of the sample solution became 90 degrees. Except for this, the experiment was carried out in the same manner as that described in <Example A-1>.

Example A-5

Amplification from 120-Degree Direction

The kit prepared in (1-5) above was used such that the angle between the developing direction of the amplification solution and the developing direction of the sample solution became 120 degrees. Except for this, the experiment was carried out in the same manner as that described in <Example A-1>.

Example A-6

Amplification from 135-Degree Direction

The kit prepared in (1-5) above was used such that the angle between the developing direction of the amplification solution and the developing direction of the sample solution became 135 degrees. Except for this, the experiment was carried out in the same manner as that described in <Example A-1>.

Example A-7

Amplification from 150-Degree Direction

The kit prepared in (1-5) above was used such that the angle between the developing direction of the amplification solution and the developing direction of the sample solution became 150 degrees. Except for this, the experiment was carried out in the same manner as that described in <Example A-1>.

Example A-8

Amplification from 170-Degree Direction

The kit prepared in (1-5) above was used such that the angle between the developing direction of the amplification solution and the developing direction of the sample solution became 170 degrees. Except for this, the experiment was carried out in the same manner as that described in <Example A-1>.

Comparative Example A-2

Amplification from 180-Degree Direction

The kit prepared in (1-5) above was used such that the angle between the developing direction of the amplification solution and the developing direction of the sample solution became 180 degrees. Except for this, the experiment was carried out in the same manner as that described in <Example A-1>.

<Results>

When compared with the results of <Comparative example A-1> amplification from 0-degree direction and the results of <Comparative example A-2> amplification from 180-degree direction, background noise was decreased after amplification in Examples A-1 to A-7, in which amplification was carried out from different angle directions. It is considered that gold used as a label substance non-specifically existing in the background was washed out by the development of the amplification solution, and that the background noise was thereby decreased. The relationship between the angle made between the developing direction of the amplification solution and the developing direction of the sample solution and the background due to a non-specifically remaining label substance is shown in FIG. 15.

The background noise was significantly decreased by amplification from an angle between 45 and 170 degrees, particularly between 60 and 150 degrees, and further particularly of 90 degrees. In the case of the sample, in which the background noise was decreased, the contrast of a detection line to the background was improved, and thus visibility was increased.

Comparative Example B-1

Amplification Time Obtained when Sample and Silver Amplification Solution are Developed in the Same Direction Preparation of Immunochromatography Kit Used in Detection of hCG
(1-1) Preparation of Anti-hCG Antibody-Modified (Immobilized) Gold Colloid 1 mL of a 50 μg/mL anti-hCG monoclonal antibody (Anti-hCG 5008 SP-5, Medix Biochemica) solution was added to a gold colloidal solution having pH adjusted by addition of 1 mL of a 50 mM $KH_2PO_4$ buffer (pH 7.0) to 9 mL of a 50-nm diameter gold colloidal solution (EM.GC50, BBI), followed by agitation. The mixture was allowed to stand for 10 minutes and then 550 μL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified (immobilized) gold colloid (50 nm) solution was obtained.
(1-2) Preparation of Gold Colloidal Antibody-Holding Pad Each of the antibody-modified (immobilized) gold colloids prepared in (1-1) above was diluted with water and a coating solution for a gold colloid (20 mM Tris-Hcl buffer (pH 8.2), 0.05% PEG (Mw: 20000), and 5% sucrose) to set the OD at 520 nm to 1.5. This solution was uniformly applied to glass fiber pads (Glass Fiber Conjugate Pad, Millipore) cut to a size of 8 mm×150 mm in an amount of 0.8 mL per pad. The pads were dried under reduced pressure overnight to obtain gold colloidal antibody-holding pads.
(1-3) Preparation of Antibody-Immobilized Membrane (Chromatographic Carrier)

An antibody-immobilized membrane was prepared in the following manner by immobilizing an antibody on a nitrocellulose membrane (HiFlow Plus HF120 with a plastic lining, Millipore) cut to a size of 25 mm×200 mm. The membrane, with one of its long sides facing downward, was coated with an anti-hCG monoclonal antibody (for immobilization) (Anti-Alpha subunit 6601 SPR-5, Medix Biochemica) solution prepared at a concentration of 0.5 mg/ml with the use of a coater of inkjet type (BioDot Ltd.). Specifically, the membrane was coated so that a linear portion thereof 8 mm above the lower edge was coated to have a width of approximately 1 mm. In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 12 mm above the lower edge was coated. The coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, and 50 mM Tris-HCl (pH 7.5) buffer) in a similar vat and then allowed to stand therein for 30 minutes. The membrane was removed from the solution and then dried overnight at room temperature to give an antibody-immobilized membrane.
(1-4) Preparation of Immunochromatography Kit The antibody-immobilized membrane prepared in (1-3) above was adhered to a back pressure-sensitive adhesive sheet 1 (ARcare9020, NIPPN TechnoCluster, Inc.). At this time, the membrane was used with the anti-hCG antibody line side (one of the long sides of the membrane) facing downward. The gold colloidal antibody-holding pad prepared in 2 above was adhered onto the antibody-immobilized membrane such that the pad overlapped the lower portion of the antibody-immobilized membrane by approximately 2 mm. The sample addition pad (glass fiber pad (Glass Fiber Conjugate Pad, Millipore) cut to a size of 5 mm×100 mm was adhered to the gold colloidal antibody-holding pad such that the sample addition pad overlapped the lower portion of the gold colloidal antibody-holding pad by approximately 5 mm. An absorbent pad (cellulose membrane cut to a size of 20 mm×150 mm (Cellulose Fiber Sample Pad, Millipore)) was adhered onto the antibody-immobilized membrane such that the absorbent pad overlapped the upper portion of the antibody-immobilized membrane by approximately 5 mm. With the use of a guillotine cutter (CM4000, NIPPN TechnoCluster, Inc.), the thus overlapped and adhered members were cut in parallel to the short sides of the overlapped members at 5-mm intervals, whereby immunochromatographic strips were prepared. These strips were placed in a plastic case (NIPPN TechnoCluster, Inc.), so as to prepare an immunochromatography kit for testing.
(1-5) Preparation of Silver Amplification Solution
(i) Preparation of Amplification Solution A-1

40 mL of a 1 mol/L iron nitrate aqueous solution produced by dissolving iron (III) nitrate nonahydrate (Wako Pure Chemical Industries, Ltd.; 095-00995) in water, 10.5 g of citric acid (Wako Pure Chemical Industries, Ltd.; 038-06925), 0.1 g of dodecylamine (Wako Pure Chemical Industries, Ltd.; 123-00246), and 0.1 g of $C_9H_{19}$—$C_6H_4$—O—$(CH_2CH_2O)_{50}H$ were dissolved in 325 g of water. After all the aforementioned components had been dissolved in the water, 40 mL of nitric acid (10% by weight) was added to the mixed solution, while stirring with a stirrer. Thereafter, 80 mL of the solution was weighed, and 11.76 g of iron (II) ammonium sulfate hexahydrate (Wako Pure Chemical Industries, Ltd.; 091-00855) was added thereto. The obtained mixture was defined as amplification solution A-1.
(ii) Preparation of Amplification Solution A-2

Water was added to 10 mL of a silver nitrate solution (containing 10 g of silver nitrate), resulting in a total amount of 100 g. This solution was defined as amplification solution A-2 (10% by weight of silver nitrate aqueous solution).

(iii) Preparation of Amplification Solution A 40 mL of amplification solution A-1 was weighed, and 4.25 mL of amplification solution A-2 was then added thereto, followed by stirring. The obtained mixture was defined as amplification solution A.

(2) Amplification Evaluation Method

To a PBS buffer that contained 1% by mass of BSA, hCG (recombinant hCG R-506; manufactured by ROHTO Pharmaceutical Co., Ltd.) was dissolved, so as to prepare hCG solutions used in tests ($1.8 \times 10^{-12}$M and $1.8 \times 10^{-13}$M).

100 µL of each hCG solution used in tests was added dropwise to each of the immunochromatography kits used in tests, and it was then left at rest for 10 minutes. Ten minutes later, each strip was removed from the plastic case, and it was than placed in a microtube that contained 500 µL of a washing solution (a PBS buffer containing 1% BSA). The strip was left as was for 1 hour, so as to wash the membrane. Thereafter, a water absorbent pad, which had previously been immobilized on the strip, was removed. Three water absorbent pads (20 mm×5 mm) were laminated on one another, and the thus laminated pads were adhered to the removed portion. The lower side of a gold colloidal antibody-holding pad was cut out, and the portion was placed downward. A sample-dropping portion was placed against the wall of a microtube (BM4020; BM Equipment Co., Ltd.) that contained 200 µL of an amplification solution A, such that the sample-dropping portion was immersed in the solution. The time at which the pad begun to absorb the amplification solution was defined as 0 minute, and amplification was carried out until the concentration of the detection line became detectable. The time was measured. The water absorbent pad was washed with water for 5 minutes immediately after completion of the amplification. The results are shown in FIG. 15.

(1-6) Measurement of Number of Label Substances at Detection Zone

A 1% BSA-containing PBS buffer was prepared. 100 µL each of the hCG solutions used in tests having concentrations of $1.8 \times 10^{-12}$M and $1.8 \times 10^{-13}$M prepared in (1-5) above was added to the immunochromatogaphy kit prepared by the method described in (1-1) to (1-4) above. Fifteen minutes later, a strip was removed from a plastic case. A portion containing a "line portion (detection portion)" with a width of 2.0 mm (wherein the line portion has a width of 1 mm and the aforementioned portion also contains a portion of 0.5 mm upstream of the line portion and a portion of 0.5 mm downstream thereof) and a "non-line portion" with a width of 2.0 mm (which is a portion located in the center of the "line portion" and a control portion) were cut out. The amount of gold existing in each portion was quantified using HR-ICP-MS (model number: Element XR; Thermo Fisher Scientific K.K.). In addition, the length of each side of the individual cut portions was measured using a vernier caliper, and the number of label substances existing only in the "line portion (detection portion)" was calculated based on the density of label substances existing in the "non-line portion."

The numbers of label substances at a detection zone in the case of adding the $1.8 \times 10^{-12}$M hCG solution used in test and the $1.8 \times 10^{-13}$M hCG solution used in test were found to be $1 \times 10^5$/mm$^3$ and $1 \times 10^4$/mm$^3$, respectively.

Comparative Example B-2

Amplification Time Required when Amplification is Carried Out by Adding Amplification Solution Dropwise An immunochromatography kit was prepared by the same operations as those described in (1-1) to (1-5) of Comparative example B-1 above. As an amplification operation, 50 µL of an amplification solution was added dropwise to a detection line portion, and the time at which the amplification solution begun to be added dropwise was defined as 0 minute. Amplification was carried out until the concentration of the detection line became detectable, and the time was measured. The water absorbent portion was washed with water for 5 minutes immediately after completion of the amplification. The results are shown in Table 2.

Comparative Example B-3

Amplification Time Required when Amplification is Carried Out by Immersion in Amplification Solution An immunochromatography kit was prepared by the same operations as those described in (1-1) to (1-5) of Comparative example B-1 above. As an amplification operation, 15 mL of an amplification solution was added to a balance dish (44 mm×44 mm×15 mm), and an immunochromatographic strip was immersed therein for amplification. The time at which the strip was immersed in the amplification solution was defined as 0 minute. Amplification was carried out until the concentration of a detection line became detectable, and the time was measured. The water absorbent pad was washed with water for 5 minutes immediately after completion of the amplification. The results are shown in Table 2.

From the results of Comparative examples B-1, B-2 and B-3, it was confirmed that the amplification time becomes shorter in the case of allowing a portion of the strip to come into contact with the amplification solution so as to absorb it by capillary action than in the case of adding the amplification solution dropwise to the detection line or the case of immersing the strip as a whole in the amplification solution.

Example B-1

Figure 8:
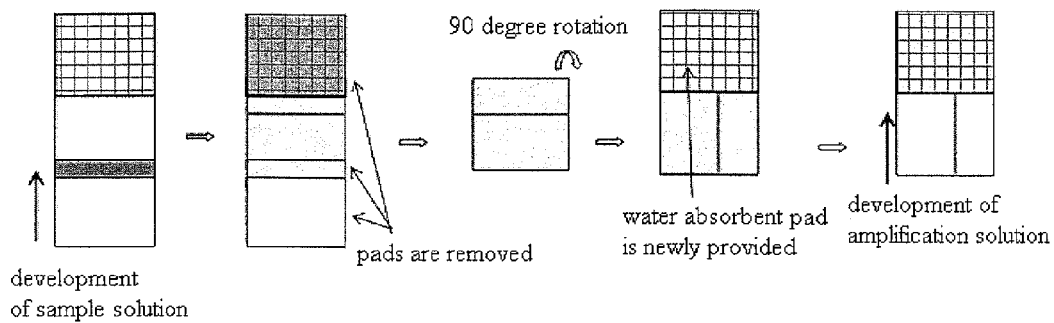
FIG. 8 shows the immunochromatographic strip used in Example B-1 and experimental operations.

Amplification Time Required when Amplification is Carried Out by Developing Sample and Silver Amplification Solution in Vertical Direction An immunochromatography kit was prepared by the same operations as those described in (1-1) to (1-3) of Comparative example B-1 above. With regard to (1-4), a strip was prepared by setting the strip width at 3 cm, and except for this, the same operation as that described in (1-4) above was carried out. An amplification operation was carried out as follows. First, a gold colloidal antibody-holding pad, a sample addition pad and an absorbent pad were removed from the immunochromatographic strip after amplification. Then, the strip was rotated 90 degrees, as shown in FIG. 8, and a new water absorbent pad (20 mm×55 mm) was attached to the top end thereof using a scotch tape. 10 mL of an amplification solution was placed in a balance dish (44 mm×44 mm×15 mm), and a strip on the side opposite to the water absorbent pad was immersed in the solution, so as to carry out amplification. The time at which the strip was placed in the amplification solution was defined as 0 minute. The amplification was carried out until the concentration of the detection line became detectable, and the time was measured. The water absorbent pad was removed immediately after completion of the amplification, and it was then washed with water for 5 minutes. The results are shown in FIG.15.

Moreover, the backside of a sample was attached to a sample support using a carbon paste, followed by carbon shadowing. Thereafter, the surface of the sample was observed by SEM utilizing a reflector voltage, using FE- STEM S-5500 manufactured by Hitachi High-Technologies Corp., at a acceleration voltage of 10 KV. Subsequently, 100 signal particles were selected, the diameter of the projected area (circle) of the particles was measured, and the mean value was then calculated. The mean particle size was found to be 2.8 µm.

Example B-2

Figure 9:
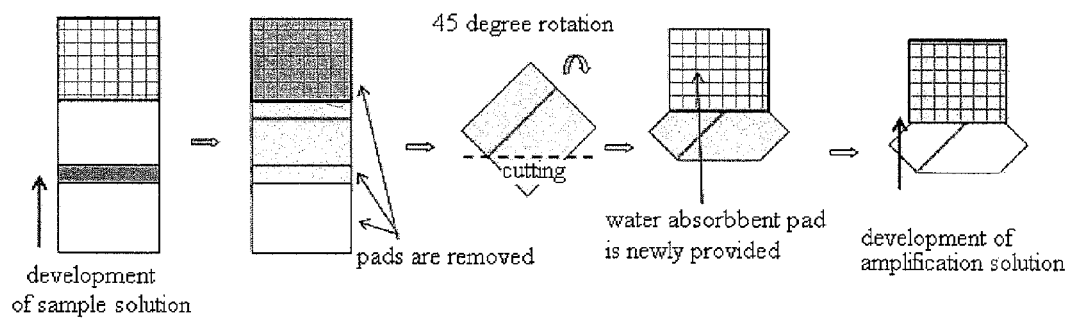
FIG. 9 shows the immunochromatographic strip used in Example B-2 and experimental operations.

Amplification Time Required when Amplification is Carried Out by Setting Angle Between Developing Direction of Sample and Developing Direction of Silver Amplification Solution at 45 Degrees An immunochromatography kit was prepared in the same manner as that described in Example B-1. An amplification operation was carried out as follows. First, a gold colloidal antibody-holding pad, a sample addition pad and an absorbent pad were removed from the immunochromatographic strip after amplification. Then, the strip was rotated 45 degrees, as shown in FIG. 9, and a new water absorbent pad (20 mm×55 mm) was attached to the top end thereof using a scotch tape. A strip on the side opposite to the water absorbent pad was cut out as shown in FIG. 9, such that it could be uniformly immersed in an amplification solution. 10 mL of the amplification solution was placed in a balance dish (44 mm×44 mm×15 mm), and the strip on the side opposite to the water absorbent pad was immersed in the solution, so as to carry out amplification. The time at which the strip was placed in the amplification solution was defined as 0 minute. The amplification was carried out until the concentration of the detection line became detectable, and the time was measured. The water absorbent pad was removed immediately after completion of the amplification, and it was then washed with water for 5 minutes. The results are shown in Table 2.

Example B-3

Amplification Time Required when Amplification is Carried Out by Setting Angle Between Developing Direction of Sample and Developing Direction of Silver Amplification Solution at 170 Degrees An immunochromatography kit was prepared in the same manner as that described in Example B-2. An amplification operation was carried out in the manner as that described in Example B-2, with the exception that the strip was rotated 170 degrees. The time at which the strip was placed in the amplification solution was defined as 0 minute. The amplification was carried out until the concentration of the detection line became detectable, and the time was measured. The water absorbent pad was removed immediately after completion of the amplification, and it was then washed with water for 5 minutes. The results are shown in Table 2.

When compared with the results of Comparative example B-1, the distance from the contact area with the amplification solution to the detection line became shorter and as a result, the amplification time was also reduced in Examples B-1, B-2, and B-3.

Comparative Example B-4

Figure 10:
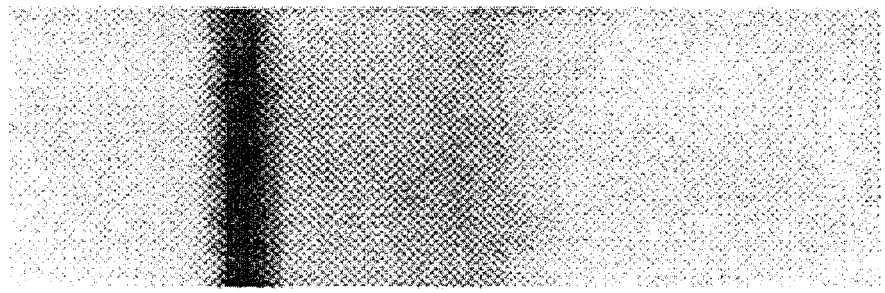
FIG. 10 shows the detection results of Comparative example B-4 and Example B-4.
Figure 10:
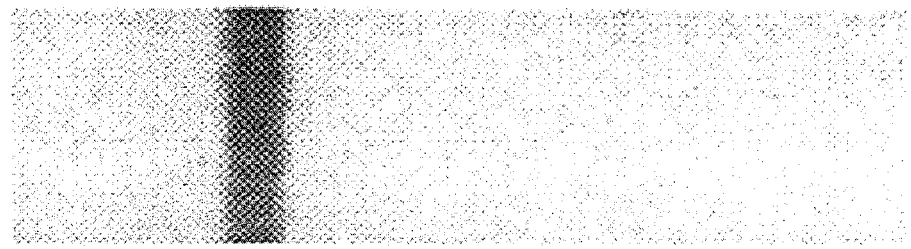

Amplification Unevenness Found in Amplification Performed by Developing Sample and Silver Amplification Solution in the Same Direction An immunochromatography kit was prepared by the same operations as those described in (1-1) to (1-5) of Comparative example B-1 above. With regard to an amplification operation, the amplification time was set at 2 minutes, and other amplification operations were carried out in the same manner as those described above. The results are shown in Table 2, and amplification unevenness was observed. The results of Comparative example B-4 are shown in FIG. 10.

Example B-4

Amplification Unevenness Found in Amplification Performed by Developing Sample and Silver Amplification Solution in Vertical Direction An immunochromatography kit was prepared by the same operations as those described in Example B-1. With regard to an amplification operation, the amplification time was set at 2 minutes, and other amplification operations were carried out in the same manner as those described above. The results are shown in Table 3, and amplification unevenness was not observed. The results of Example B-4 are shown in FIG. 10.

TABLE 2

|  | Comparative example 1 | Comparative example 2 | Comparative example 3 | Example 1 | Example 2 | Example 3 |
| --- | --- | --- | --- | --- | --- | --- |
| Time required until line is detected after $1.8 \times 10^{12}$M antigen has been added | 1 min | 1 min 30 sec | 1 min 15 sec | 30 sec | 35 sec | 35 sec |
| Time required until line is detected after $1.8 \times 10^{13}$M antigen has been added | 1 min 30 sec | 2 min | 1 min 45 sec | 45 sec | 50 sec | 50 sec |

TABLE 3

|  | Comparative example B-4 | Example B-4 |
| --- | --- | --- |
| Amplification unevenness | Observed | Not Observed |

Example C (1) Preparation of Immunochromatography Kit Used in Detection of Influenza Types A and B
(1-1) Preparation of Anti-Influenza Types A and B Antibodies-Modified (Immobilized) Gold Colloids
(1-1-1) Preparation of Anti-Influenza Type A Antibody-Modified (Immobilized) Gold Colloid 1 mL of a 90 µg/mL anti-influenza type A monoclonal antibody (Anti-Influenza A SPTN-5 7307, Medix Biochemica) solution was added to a gold colloidal solution having pH adjusted by addition of 1 mL of a 50 mM $KH_2PO_4$ buffer (pH 7.0) to 9 mL of a 50-nm diameter gold colloidal solution (EM.GC50, BBI), followed by agitation. The mixture was allowed to stand for 10 minutes and then 550 μL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA Fraction V, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified (immobilized) gold colloid (50 nm) solution was obtained.

(1-1-2) Preparation of Anti-Influenza Type B Antibody-Modified (Immobilized) Gold Colloid 1 mL of a 80 μg/mL anti-influenza type B monoclonal antibody (MONOTOPE aby Influenza B Virus (nuclear) Purified 1131, ViroStat, Inc.) solution was added to a gold colloidal solution having pH adjusted by addition of 1 mL of a 50 mM $KH_2PO_4$ buffer (pH 8.0) to 9 mL of a 50-nm diameter gold colloidal solution (EM.GC50, BBI), followed by agitation. The mixture was allowed to stand for 10 minutes and then 550 μL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified (immobilized) gold colloid (50 nm) solution was obtained.

(1-2) Preparation of Gold Colloidal Antibody-Holding Pad

The influenza type A and B antibodies-modified (immobilized) gold colloids prepared in (1-1) above were mixed at an OD ratio of 1:1, and the mixture was then diluted with water and a coating solution for a gold colloid (20 mM Tris-Hcl buffer (pH 8.2), 0.05% PEG (Mw: 20000), and 5% sucrose) to set the OD at 520 nm to 3.0. This solution was uniformly applied to glass fiber pads (Glass Fiber Conjugate Pad, Millipore) cut to a size of 8 mm×150 mm in an amount of 0.8 mL per pad. The pads were dried under reduced pressure overnight to obtain gold colloidal antibody-holding pads.

(1-3) Preparation of Antibody-Immobilized Membrane (Chromatographic Carrier)

An antibody-immobilized membrane was prepared in the following manner by immobilizing an antibody on a nitrocellulose membrane (HiFlow Plus HF120 with a plastic lining; membrane thickness: approximately 0.13 mm; Millipore) cut to a size of 25 mm×200 mm. The membrane, with one of its long sides facing downward, was coated with an anti-influenza A monoclonal antibody for immobilization (Anti-Influenza A SPTN-5 7307, Medix Biochemica) solution prepared at a concentration of 1.5 mg/ml with the use of a coater of inkjet type (BioDot Ltd.). Specifically, the membrane was coated so that a linear portion thereof 7 mm above the lower edge was coated to have a width of approximately 0.7 mm. Likewise, the membrane was coated with an anti-influenza B monoclonal antibody for immobilization (MONOTOPE aby Influenza B Virus (nuclear) Purified 1131, ViroStat, Inc.) solution prepared at a concentration of 1.5 mg/ml with the use of a coater of inkjet type (BioDot Ltd.). Specifically, the membrane was coated so that a linear portion thereof 10 mm above the lower edge was coated to have a width of approximately 0.7 mm. In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 13 mm above the lower edge was coated. The coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, and 50 mM Tris-HCl (pH 7.5) buffer) in a similar vat and then allowed to stand therein for 30 minutes. The membrane was removed from the solution and then dried overnight at room temperature to give an antibody-immobilized membrane.

(1-4) Assembling of Immunochromatography Kit

The antibody-immobilized membrane prepared in (1-3) above was adhered to a back pressure-sensitive adhesive sheet 1 (ARcare9020, NIPPN TechnoCluster, Inc.). At this time, the membrane was used with the anti-influenza A antibody line side (one of the long sides of the membrane) facing downward. The gold colloidal antibody-holding pad prepared in 2 above was adhered onto the antibody-immobilized membrane such that the pad overlapped the lower portion of the antibody-immobilized membrane by approximately 2 mm. The sample addition pad (glass fiber pad (Glass Fiber Conjugate Pad, Millipore) cut to a size of 18 mm×150 mm) was adhered to the gold colloidal antibody-holding pad such that the sample addition pad overlapped the lower portion of the gold colloidal antibody-holding pad by approximately 4 mm. An absorbent pad (cellulose glass membrane cut to a size of 80 mm×150 mm (CF6, Whatman)) was adhered onto the antibody-immobilized membrane such that the absorbent pad overlapped the upper portion of the antibody-immobilized membrane by approximately 5 mm. With the use of a guillotine cutter (CM4000, NIPPN TechnoCluster, Inc.), the thus overlapped and adhered members (members that constitute a main body of the immunochromatography kit) were cut in parallel to the short sides of the overlapped members at 15-mm intervals, whereby 15 mm×55 mm immunochromatographic strips were prepared. An immunochromatography kit for testing was prepared with these strips.

(1-5) Washing Solution

A 1% BSA-containing PBS buffer prepared by dissolving 1% by weight of BSA (Sigma) in a PBS buffer (Wako Pure Chemical Industries, Ltd.) was used as a washing solution.

(1-6) Preparation of Silver Amplification Solution
(1-6-1) Preparation of Amplification Solution A
(1-6-1-1) Preparation of Amplification Solution A-1

40 mL of a 1 mol/L iron nitrate aqueous solution produced by dissolving iron (III) nitrate nonahydrate (Wako Pure Chemical Industries, Ltd.; 095-00995) in water, 10.5 g of citric acid (Wako Pure Chemical Industries, Ltd.; 038-06925), 0.1 g of dodecylamine (Wako Pure Chemical Industries, Ltd.; 123-00246), and 0.44 g of a surfactant, $C_9H_{19}$—$C_6H_4$—O—$(CH_2CH_2O)_{50}H$ were dissolved in 325 g of water. After all the aforementioned components had been dissolved in the water, 40 mL of nitric acid (10% by weight) was added to the mixed solution, while stirring with a stirrer. Thereafter, 80 mL of the solution was weighed, and 11.76 g of iron (II) ammonium sulfate hexahydrate (Wako Pure Chemical Industries, Ltd.; 091-00855) was added thereto. The obtained mixture was defined as amplification solution A-1.

(1-6-1-2) Preparation of Amplification Solution A-2

Water was added to 10 mL of a silver nitrate solution (containing 10 g of silver nitrate), resulting in a total amount of 100 g. This solution was defined as amplification solution A-2 (10% by weight of silver nitrate aqueous solution).

(1-6-1-3) Preparation of Amplification Solution A 40 mL of amplification solution A-1 was weighed, and 4.25 mL of amplification solution A-2 was then added thereto, followed by stirring. The obtained mixture was defined as amplification solution A.

(2) Evaluation

Comparative Example C-1

Washing from 0-Degree Direction (2-1) Washing with Washing Solution

A quick S-influ A·B "Seiken" negative/positive control (product No. 322968; DENKA SEIKEN Co., Ltd.) was used as a sample solution. This positive control solution was diluted with a PBS buffer containing 1% by mass of BSA. The detection limit of both type A and B was 1/40, when a commercially available immunochromatography kit "Capillia Flu A+B" (Alfresa Pharma Corp.) was used. This time, this positive control was diluted to 1/200 with a PBS buffer containing 1% by mass of BSA, and the obtained solution was used as a sample solution.

300 μL of the sample solution was added dropwise to the sample addition pad of the immunochromatography kit used for tests, which had been prepared in (1-4) above, such that the sample solution could be uniformly applied on the pad. Thereafter, it was left at rest for 10 minutes. This time, the applied concentration was less than the detection limit concentration (1/40 diluted solution even in the case of the present kit), and thus a detection line could not be confirmed by visual observation. This membrane was removed from the case, and a sample pad and a water absorbent pad were removed. A straight line that connected a washing solution addition pad and a water absorbent pad was allowed to pass a point located in the center from both ends of a strip in an area between two capturing portions (TL), so that the angle between the developing direction of the washing solution and the developing direction of the sample solution became 0 degree. A washing solution addition pad (glass fiber pad (Glass Fiber Conjugate Pad, Millipore) cut to a size of 18 mm×8 mm), to which a back adhesive sheet with a size of 13 mm×8 mm (ARcare 9020; NIPPN TechnoCluster, Inc.) had been adhered, was attached with a tape to the upstream tip of the developed washing solution, whereas a water absorbent pad (cellulose membrane (CF6; Whatman) cut to a size of 100 mm×8 mm), to which a back adhesive sheet with a size of 95 mm×8 mm (ARcare 9020; NIPPN TechnoCluster, Inc.) had been adhered, was attached with a tape to the downstream tip thereof. The washing solution addition pad was placed into a rectangular container (9 mm long×64 mm wide×25 mm high) that contained 10 mL of a washing solution, such that the washing solution addition pad was immersed in the solution. Thus, a washing operation was carried out for 10 minutes. Thereafter, the water absorbent pad was removed, and the weight was measured. Subsequently, the pad was dried by vacuum drying for 1 hour, so that the water content was completely dried. After the pad was dried, the weight was measured again, and the weight of the pad after drying was subtracted from the weight of the pad before drying, so as to measure the water content of the water absorbent pad. As a result, the amount of the washing solution absorbed by the pad was found to be 96 mg. When the gravity of the washing solution was defined as 1, the amount of the washing solution absorbed was 96 mL. This amount was estimated to be the amount of the washing solution supplied. With regard to the width of a flow channel, it was considered that such a washing solution was added to the entire surfaces of the water absorbent pad and the washing solution addition pad, and that the washing solution was supplied to a flow channel of 8 mm that corresponded to the width of the water absorbent pad. Hence, the flow rate per minute per mm of a developing flow channel was obtained to be 96/(10×8)=1.2 μL/min·mm. The thus obtained flow rate was defined as the flow rate of the washing solution.

In the present experiment, the height of a liquid face that depended on the form of a washing solution container during the washing operation, the form and material of the sample addition pad of an immunochromatography kit, an experimental environment (temperature and humidity), the material and thickness of the absorbent pad, connection of the absorbent pad with a nitrocellulose membrane, and the like are factors for changing the water-absorbing speed and the amount of the washing solution absorbed. Thus, it is necessary to keep these factors constant in the experiment. The washing water-absorbing speed and the amount of the washing solution absorbed are factors for determining the final washing effect (a decrease in the remaining amount of gold fine particles). This experiment was carried out at an air temperature of 22±3 C.° and a humidity of 50±15%.

(2-2) Signal Amplification with Amplification Solution and Background Evaluation The water absorbent pad was eliminated, and the membrane was then immersed in a plastic tray containing 40 mL of the amplification solution A prepared in (1-6) above. While stirring with a stirrer, silver amplification was carried out for 2 minutes. This membrane was removed from the amplification solution, and it was then well washed with water for 3 minutes. Thereafter, the membrane was subjected to measurement using a concentration measurement apparatus for immunochromatography (ICA-1000; Hamamatsu Photonics K.K.) so as to measure an optical concentration reflecting to a reference white board. This measurement was carried out twice, and the average value was then rounded off to the fourth decimal place. The obtained value was defined as a background measurement result. As a measurement position, a point located in the center from both ends of a membrane in an area between the two capturing portions (TL) of the membrane was measured. The thus obtained concentrations were defined as background concentrations, and they are shown in FIG. 15.

Moreover, the concentration of a membrane after amplification, to which no gold colloids had been supplied, and the concentration of a membrane after amplification, on which no washing operations had been performed in (2-1) above are also shown in the table. A value obtained by subtracting this value from each measured background concentration was considered to be background caused by background gold due to remaining gold, and it is also shown in FIG. 15.

(2-3) Evaluation of Ease of Seeing Line

The ease of seeing a detection line amplified in (2-2) above was evaluated using the symbols ⊚, ○, Δ, × and ×× (invisible) in the order that the contrast of the detection line to the background was clear and thus that the line was easily seen. The results are shown in FIG. 16.

Example C-1

Washing from 30-Degree Direction

The angle between the direction of the washing solution and the developing direction of the sample solution was set at 30 degrees in (2-1) above. Except this, the experiment was carried out in the same manner as that in (2-1) to (2-3) above. The flow rate of the washing solution was 1.2 µL/min·mm.

Example C-2

Washing from 45-Degree Direction

The angle between the direction of the washing solution and the developing direction of the sample solution was set at 45 degrees in (2-1) above. Except this, the experiment was carried out in the same manner as that in (2-1) to (2-3) above. The flow rate of the washing solution was 1.3 µL/min·mm.

Example C-3

Washing from 60-Degree Direction

The angle between the direction of the washing solution and the developing direction of the sample solution was set at 60 degrees in (2-1) above. Except this, the experiment was carried out in the same manner as that in (2-1) to (2-3) above. The flow rate of the washing solution was 1.3 µL/min·mm.

Example C-4

Washing from 90-Degree Direction

The angle between the direction of the washing solution and the developing direction of the sample solution was set at 90 degrees in (2-1) above. Except this, the experiment was carried out in the same manner as that in (2-1) to (2-3) above. The flow rate of the washing solution was 1.6 µL/min·mm.

Example C-5

Washing from 120-Degree Direction

The angle between the direction of the washing solution and the developing direction of the sample solution was set at 120 degrees in (2-1) above. Except this, the experiment was carried out in the same manner as that in (2-1) to (2-3) above. The flow rate of the washing solution was 1.4 µL/min·mm.

Example C-6

Washing from 135-Degree Direction

The angle between the direction of the washing solution and the developing direction of the sample solution was set at 135 degrees in (2-1) above. Except this, the experiment was carried out in the same manner as that in (2-1) to (2-3) above. The flow rate of the washing solution was 1.4 µL/min·mm.

Example C-7

Washing from 150-Degree Direction

The angle between the direction of the washing solution and the developing direction of the sample solution was set at 150 degrees in (2-1) above. Except this, the experiment was carried out in the same manner as that in (2-1) to (2-3) above. The flow rate of the washing solution was 1.3 µL/min·mm.

Example C-8

Washing from 170-Degree Direction

The angle between the direction of the washing solution and the developing direction of the sample solution was set at 170 degrees in (2-1) above. Except this, the experiment was carried out in the same manner as that in (2-1) to (2-3) above. The flow rate of the washing solution was 1.2 µL/min·mm.

Example C-9

Washing from 180-Degree Direction

The angle between the direction of the washing solution and the developing direction of the sample solution was set at 180 degrees in (2-1) above. Except this, the experiment was carried out in the same manner as that in (2-1) to (2-3) above. The flow rate of the washing solution was 1.2 µL/min·m.

<Results>

Figure 12:
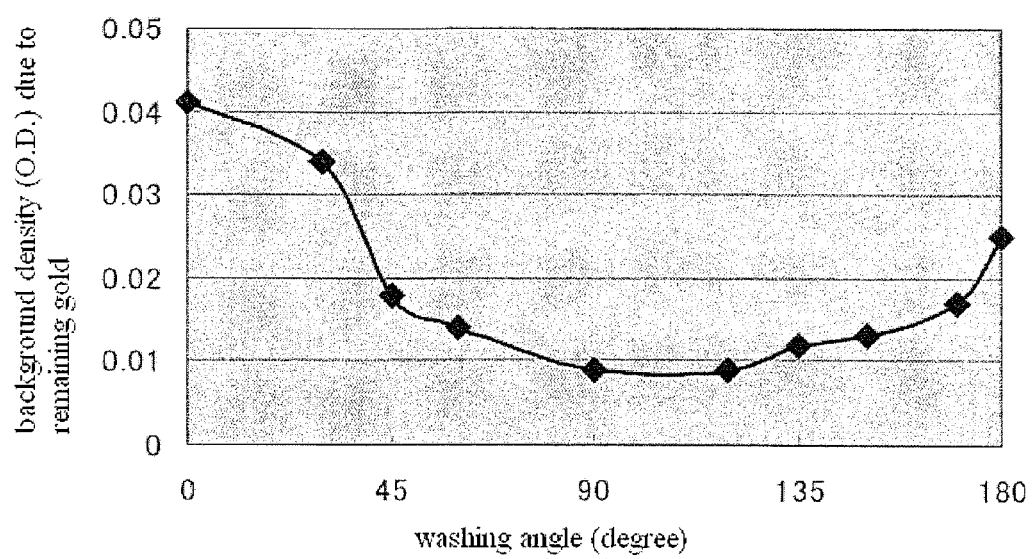
FIG. 12 shows the relationship between a washing angle and background caused by a non-specifically remaining label substance.

When compared with washing from a 0-degree direction, background noise was decreased after washing in all of Examples 1 to 9, wherein washing was carried out from each different angles. This may be because gold as a label substance non-specifically existing in the background was washed off by washing, and because background noise was decreased after amplification. The relationship between such washing angle and the background in which a label substance non-specifically remains is shown in FIG. 12.

Such background noise was significantly decreased at an angle of particularly 45 to 170 degrees, more particularly 60 to 170 degrees, and further particularly 60 to 135 degrees. In the case of a sample in which background noise was decreased, the contrast of a detection line to the background was improved, and thus visibility was increased.

Washing with Reducing Agent Solution

Example C-10

Washing with Amplification Solution Containing Reducing Agent from 90-Degree Direction The angle between the developing direction of the washing solution and the developing direction of the sample solution was set at 90 degrees in (2-1) above. As a washing solution, amplification solution A-1 containing a reducing agent component that is one type of amplification solution, as described in (1-6-1-1) above, was used. Except this, the experiment was carried out in the same manner as that in (2-1) to (2-3) above. The flow rate of the washing solution was 1.4 µL/min·mm.

Comparative Example C-2

Washing with Buffer from 90-Degree Direction

Figure 13:
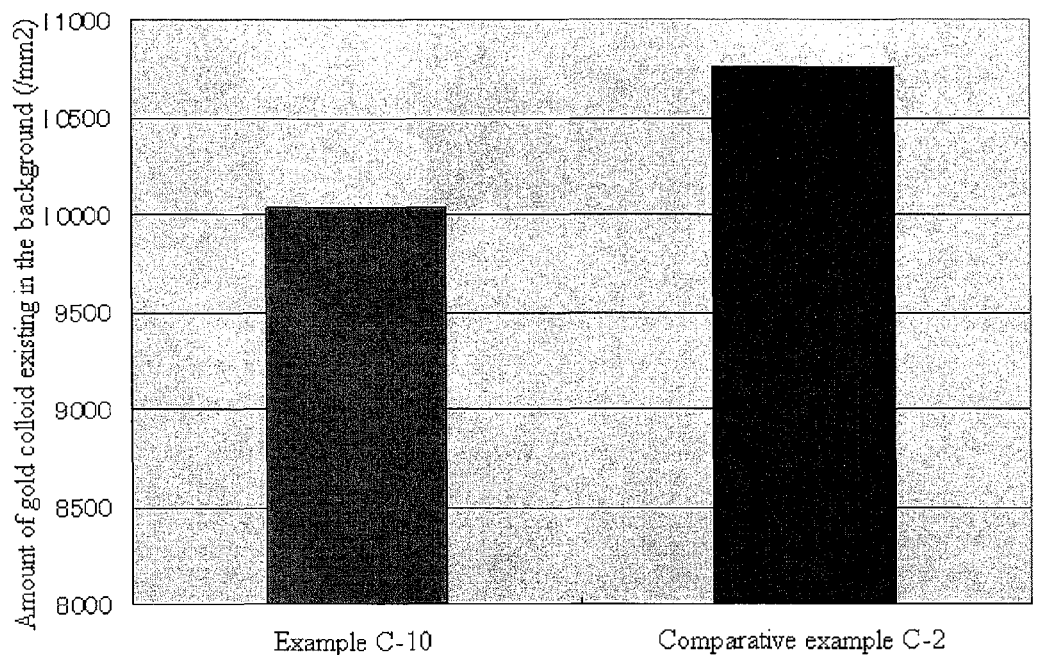
FIG. 13 shows the results obtained by measuring the amount of gold in the background in each of the case of washing with a reducing agent contained in an amplification solution and the case of washing with a buffer.

The angle between the developing direction of the washing solution and the developing direction of the sample solution was set at 0 degree in (2-1) above. Except this, the experiment was carried out in the same manner as that in (2-1) to (2-3) above. The flow rate of the washing solution was 1.6 µL/min·mm.
<Results>
With regard to the amount of gold existing in the background after washing, after a predetermined washing operation had been carried out, a section with a width of 2 mm on the downstream side of an antibody-immobilized membrane at a zone (capturing zone) to which the antibody had been applied was cut out, and gold was then extracted with aqua regia. Thereafter, the absolute amount of the gold was quantified using a High Resolution ICP Mass Spectrometer (HR-ICP-MS). By setting the particle diameter of a gold colloid at 50 nm, the obtained gold amount was converted to the number of gold colloids. The results are shown in FIG. 13. When a washing operation was performed from an angle of 90 degrees and the washing solution was then washed with a reducing agent solution as one type of amplification solution, the amount of gold in the background could be further decreased.
Washing Time and Washing Example C-11

The angle between the developing direction of the washing solution and the developing direction of the sample solution was set at 90 degrees in (2-1) above. The washing time was set at 0 second, 5 seconds, 10 seconds, 30 seconds, 60 seconds, 180 seconds, 300 seconds, 420 seconds, and 600 seconds.

Comparative Example C-3

Figure 14:
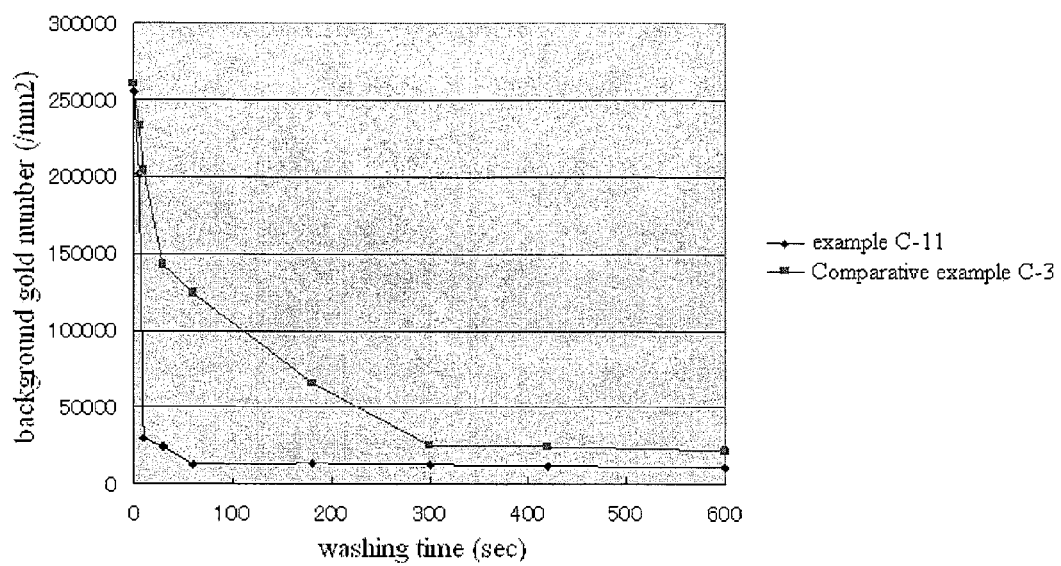
FIG. 14 shows the results obtained by measuring a washing effect obtained when a washing time is changed.

The angle between the developing direction of the washing solution and the developing direction of the sample solution was set at 0 degree in (2-1) above. The washing time was set at 0 second, 5 seconds, 10 seconds, 30 seconds, 60 seconds, 180 seconds, 300 seconds, 420 seconds, and 600 seconds.
<Results>
With regard to the amount of gold in the background after washing, after a predetermined washing operation had been carried out, a section with a width of 2 mm on the downstream side of an antibody-immobilized membrane at a zone (capturing zone) to which the antibody had been applied was cut out, and gold was then extracted with aqua regia. Thereafter, the absolute amount of the gold was quantified using a High Resolution ICP Mass Spectrometer (HR-ICP-MS). By setting the particle diameter of a gold colloid at 50 nm, the obtained gold amount was converted to the number of gold colloids. The results are shown in FIG. 14. In the case of Example C-11, the washing operation could be carried out faster than in Comparative example C-3, and the remaining gold amount could be reduced to ⅛ or less for 10 seconds.

Further, with regard to Example C-11, amplification was carried out by the method described in (2-2) above, and the obtained test line was evaluated by visual observation. Specifically visibility was evaluated using the symbols ⊚, ○, Δ, × and ×× (invisible) in the order that the test line was clearly seen. The results are shown in Table 5. A decrease in sensitivity began to occur in the washing operation for 420 seconds or more. It is considered that the overflow of gold specifically trapped by the test line took place due to excessive washing.

TABLE 5

| Dilute concentration of antigen solution | Visual evaluation | | | | | | | | |
|---|---|---|---|---|---|---|---|---|---|
| | Washing time (sec.) | | | | | | | | |
| | 0 | 5 | 10 | 30 | 60 | 180 | 300 | 420 | 600 |
| 1/200 | ×× | ×× | ○ | ⊚ | ⊚ | ⊚ | ⊚ | ⊚ | ⊚ |
| 1/400 | ×× | ×× | ○ | ⊚ | ⊚ | ⊚ | ⊚ | ○ | ○ |
| 1/1200 | ×× | ×× | ×× | ○ | ○ | ○ | ○ | ○ | ○ |
| 1/4000 | ×× | ×× | ×× | ×× | ○ | ○ | ○ | ×× | ×× |
| 1/8000 | ×× | ×× | ×× | ×× | ×× | ×× | ×× | ×× | ×× |

The invention claimed is:

1. An immunochromatography kit comprising:
   (i) an immunochromatographic strip, wherein a sample addition pad, a detection zone, and a water absorbent portion (a) are provided in that order on a chromatographic carrier, and a second binding substance that binds to an analyte to be detected, the analyte, or a compound having a portion similar to the analyte is immobilized on the detection zone; and
   (ii) an amplification solution-developing strip, wherein an amplification solution addition pad and a water absorbent portion (b) are provided in that order on an amplification solution-developing carrier,
   wherein (i) and (ii) overlap in such manner that the immunochromatographic strip intersects with the amplification solution-developing strip at an angle of 45 to 170 degrees,
   and wherein the detection zone of the immunochromatographic strip is located on a portion of the amplification solution-developing strip between the amplification solution addition pad and the water absorbent portion (b).

2. The kit according to claim 1, further comprising a first binding substance that binds to the analyte, wherein the first binding substance is labeled with a label substance.

3. The kit according to claim 2, wherein a label compound-holding pad is further provided on the chromatographic carrier between the sample addition pad and the detection zone, and the labeled first binding substance is contained in said label compound-holding pad.

4. The kit according to claim 2, wherein the first binding substance and/or the second binding substance is an antibody.

5. The kit according to claim 2, wherein the label substance comprises a metal colloid.

6. The kit according to claim 1, further comprising an amplification solution that contains a silver-containing compound and/or a reducing agent for silver.

7. The kit according to claim 1, further comprising a washing solution.

8. The kit according to claim 1, wherein any other pads and detection zones are not provided upstream of the sample addition pad in the immunochromatographic strip, and any other pads are not provided upstream of the amplification solution addition pad in the amplification solution-developing strip.

9. The kit according to claim 8, wherein the sample addition pad is provided at one end of the immunochromatographic strip while the water absorbent portion (a) is provided at the other end of the immunochromatographic strip, and the amplification solution addition pad is provided at one end of the amplification solution-developing strip while the water absorbent portion (b) is provided at the other end of the amplification solution-developing strip.

* * * * *